(12) United States Patent
Chen et al.

(10) Patent No.: US 11,653,957 B2
(45) Date of Patent: May 23, 2023

(54) SPINE PROTECTION DEVICE

(71) Applicant: Orion Spine Inc., Taipei (TW)

(72) Inventors: Thomas Chen, La Canada, CA (US); Ming-Fu Chiang, Taipei (TW)

(73) Assignee: Orion Spine Inc., Taipei (TW)

( * ) Notice: Subject to any disclaimer, the term of this patent is extended or adjusted under 35 U.S.C. 154(b) by 0 days.

(21) Appl. No.: 17/007,358

(22) Filed: Aug. 31, 2020

(65) Prior Publication Data

US 2020/0397484 A1   Dec. 24, 2020

Related U.S. Application Data

(63) Continuation of application No. 15/523,613, filed as application No. PCT/IB2016/001576 on Oct. 3, 2016, now Pat. No. 10,792,077.

(60) Provisional application No. 62/364,621, filed on Jul. 20, 2016, provisional application No. 62/235,667, filed on Oct. 1, 2015.

(51) Int. Cl.
  *A61B 17/70*  (2006.01)
  *A61B 17/00*  (2006.01)
  *A61B 17/56*  (2006.01)

(52) U.S. Cl.
  CPC .......... *A61B 17/7067* (2013.01); *A61B 17/70* (2013.01); *A61B 17/705* (2013.01); *A61B 17/7032* (2013.01); *A61B 17/7037* (2013.01); *A61B 17/7049* (2013.01); *A61B 17/7052* (2013.01); *A61B 17/7053* (2013.01); *A61B 17/7068* (2013.01); *A61B 17/7002* (2013.01); *A61B 2017/00991* (2013.01); *A61B 2017/561* (2013.01); *A61B 2017/567* (2013.01)

(58) Field of Classification Search
  CPC ............ A61B 17/7067; A61B 17/7068; A61B 17/7071; A61B 17/7059; A61B 17/7062
  See application file for complete search history.

(56) References Cited

U.S. PATENT DOCUMENTS

| | | | | |
|---|---|---|---|---|
| 9,526,533 | B1* | 12/2016 | Aranibar | A61B 17/7011 |
| 2002/0123750 | A1* | 9/2002 | Eisermann | A61F 2/441 |
| | | | | 606/76 |
| 2008/0281361 | A1* | 11/2008 | Vittur | A61B 17/7052 |
| | | | | 606/100 |
| 2009/0326592 | A1* | 12/2009 | Butler | A61B 17/7058 |
| | | | | 606/280 |
| 2013/0053893 | A1* | 2/2013 | Gamache | A61B 17/864 |
| | | | | 606/279 |

\* cited by examiner

*Primary Examiner* — Julianna N Harvey
(74) *Attorney, Agent, or Firm* — Leason Ellis LLP

(57) ABSTRACT

A surgical kit includes a shield for covering a portion of the spine of a subject. The shield can include an attachment portion adapted to engage a bone fixation assembly which is adapted to be fixed on multiple vertebra bones of the subject. The bone fixation assembly can include a vertebra joining member secured between two bone anchors. Each bone anchor can include a fastener portion adapted to be implanted into a vertebra bone and a head coupling portion adapted to secure the vertebra joining member. The shield can be coupled to the bone fixation assembly via separate coupling elements, such as a clip or an adjustable link secured between two vertebra joining members of the bone fixation assembly. Alternatively, the shield can include an integral attachment portion configured to engage the bone fixation assembly directly.

14 Claims, 17 Drawing Sheets

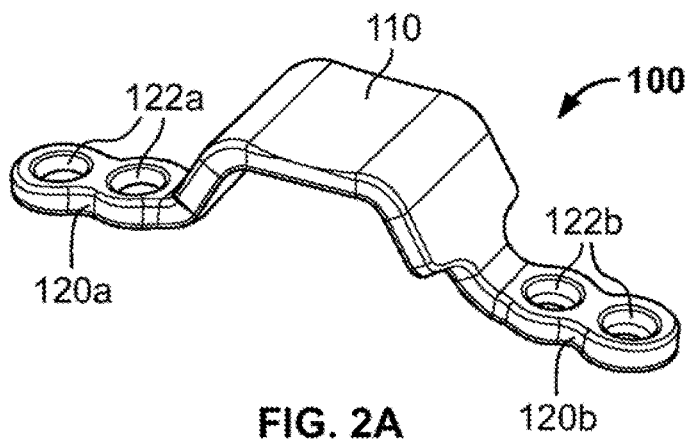
FIG. 2A
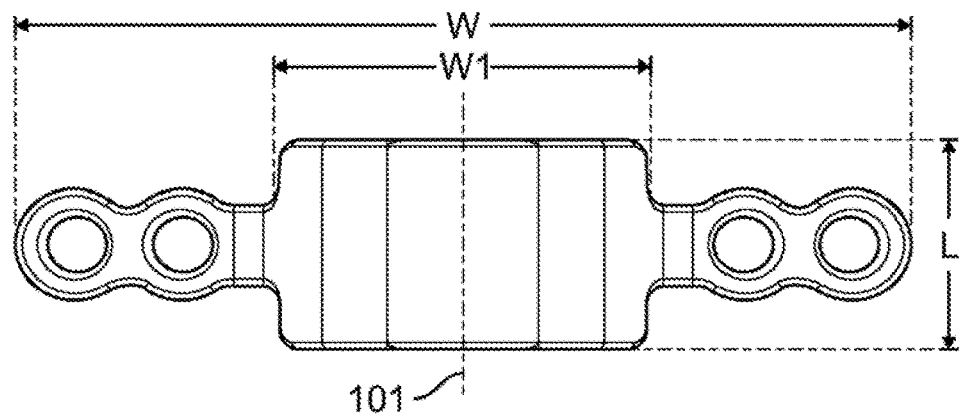
FIG. 2B
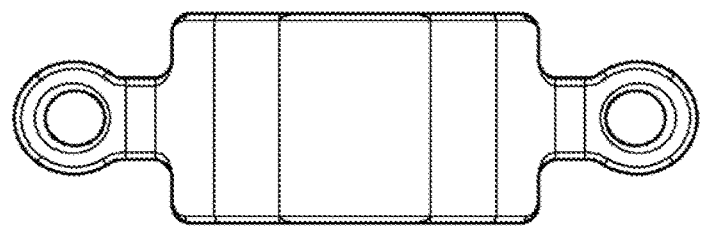
FIG. 2C
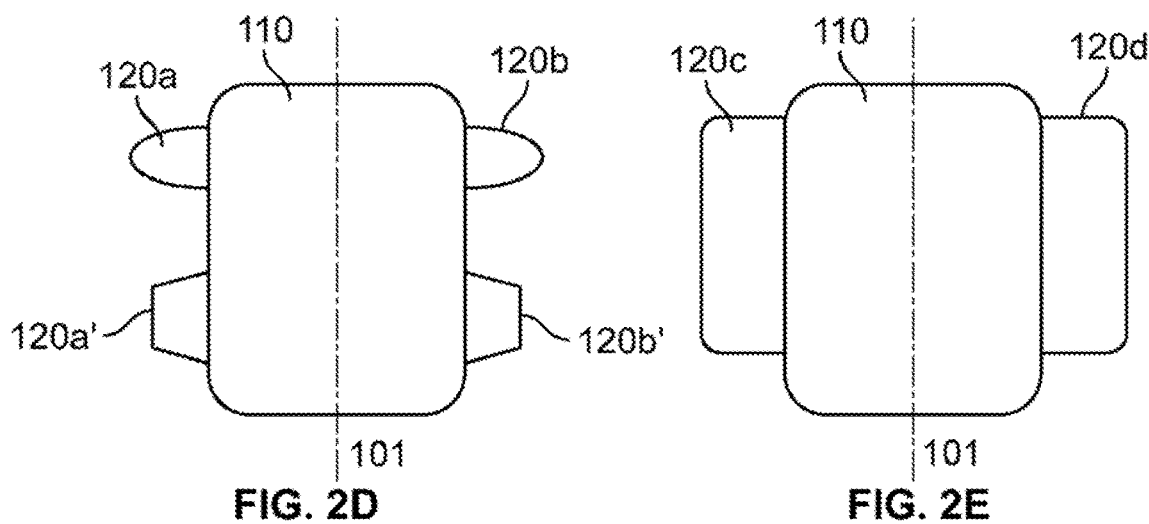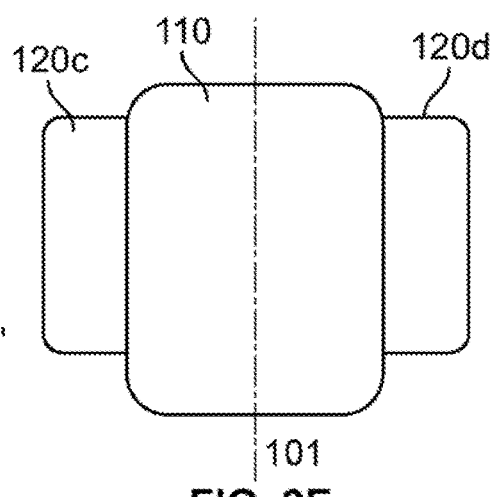
FIG. 2D  FIG. 2E

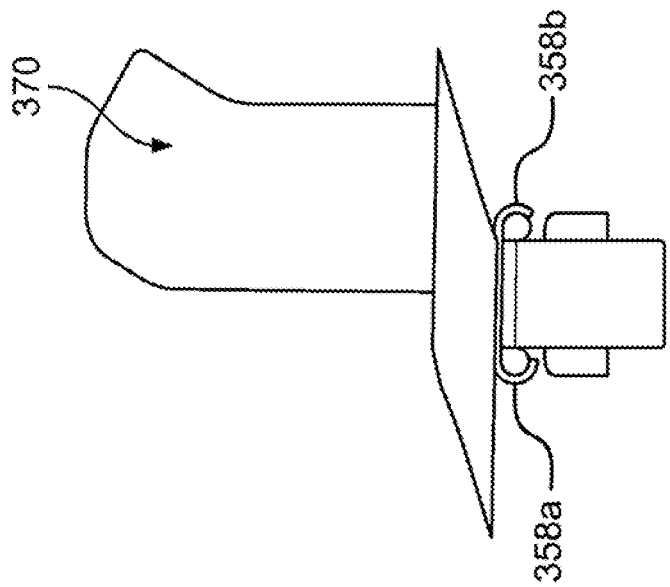
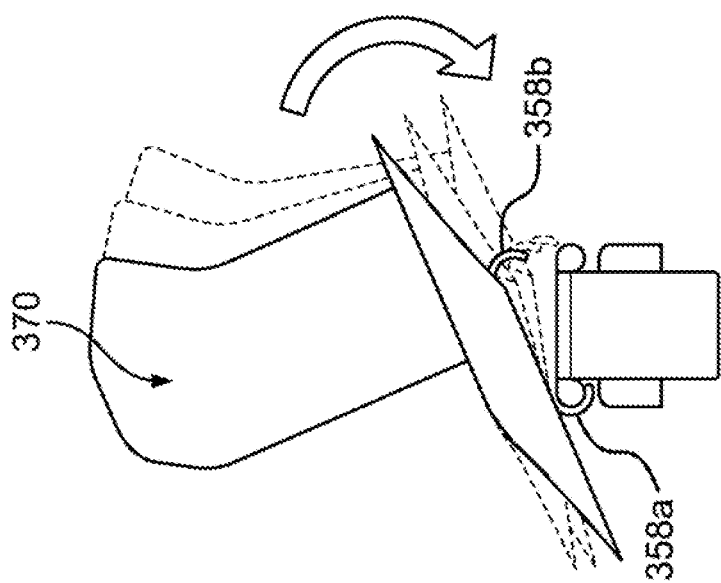

SPINE PROTECTION DEVICE

PRIORITY

This application is a continuation application of U.S. patent application Ser. No. 15/523,613, which is a U.S. National Phase Application under 35 U.S.C. § 371 of International Patent Application No. PCT/IB2016/001576, filed Oct. 3, 2016, which claims the benefit of U.S. Provisional Application Nos. 62/235,667 (filed Oct. 1, 2015) and 62/364,621 (filed Jul. 20, 2016).

The references cited in this specification, and their references, are incorporated by reference herein in their entirety where appropriate for teachings of additional or alternative details, features, and/or technical background.

FIELD OF THE INVENTION

This invention relates to spinal implant. More particularly, the invention relates to a spinal device for protection of a person's spine after laminectomy.

BACKGROUND

A laminectomy is a surgical procedure that removes a portion of the vertebral bone called the lamina—the back part of the vertebra that covers a person's spinal canal. Also known as decompression surgery, laminectomy enlarges the spinal canal to relieve pressure on the spinal cord or nerves (the pressure is most commonly caused by bony overgrowths within the spinal canal, which can occur in people who have arthritis in their spines).

There are several unfortunate consequences of laminectomies performed worldwide that have not yet been addressed. First, the laminectomy removes the protective posterior element of the spine. As a result, the patient is left with only closed paraspinal muscle, fascia, subcutaneous, tissue, and skin closure. Although the lamina is not considered an essential supportive component of the spine, loss of the lamina results in the theoretical possibility of direct injury to nervous tissue in the operated area. In the lumbar spine, there is often enough protection from the muscle and fascia; however, in the cervical spine this paraspinal musculature is limited. Secondly, scar tissue sets-in after a laminectomy, as the paraspinal muscles closed over the dura forms a fibrotic layer over it. Scar tissue surrounding the dura and nerve roots can compress the nerve roots and cauda equine, producing neural complications such as persistent, low back pain, sciatica, and/or bowel and bladder dysfunction. Third, revision surgery may prove necessary due to recurrent disk herniation, post-operative spinal stenosis (iatrogenic or acquired), or because of exuberant epidural fibrosis. As a result, repeat exposure requires going through the previous operative site without the help of normal landmarks and protection of the pre-existing lamina. In such cases, there is a greater chance of the surgeon injuring the dura, resulting in a cerebrospinal (CSF) leak. Cosmetically, as the wound contracts, the patient is left with a distinct contracture dimple or cavity that is often seen over the surgical site. This "dimple" is often cosmetically undesirable, particularly in thin patients, especially over the cervical or thoracic spine.

U.S. Pat. No. 6,454,767 discloses a spinal protection device or kit for reducing formation of post-operative adhesions. The device includes a fenestrated shield adapted to cover a bony dissection in the spine of a vertebrate. The shield can include an elongate cavity and can include attachment ports proximate to an edge of the shield to accept attachment pins, as well as a plurality of attachment pins for attaching the shield to bone. FIG. 1A is an illustration of a laminectomy of the fifth lumbar vertebrae according to U.S. Pat. No. 6,454,767. The spinal cord 24 is surrounded by a vertebral column composed of individual lumbar vertebrae 26, each composed of a transverse process 30 and a spinous process 32, and lamina 40. One of the vertebrae has been subjected to laminectomy (the cut cross section is shown in hatched lines). FIG. 1B is an illustration of a shield 10 installed on the lumbar vertebrae, where shield 10 is positioned over the laminectomy site. The attachment flats 18 are attached to the spinal processes, and a set of four attachment pins 20 are used to anchor the four corners of the shield 10 in place to the surrounding vertebrae tissue.

There is a need for an improved spine protection device that has the following desirable properties:
1) Provides protection of the spinal cord or associated nerve roots after a laminectomy.
2) Prevents postoperative scarring from healing fibroblasts on top of the dura.
3) Provides easy landmark so that the surgeon does not get into the dura and causes a CSF leak during exposure for redo surgery.
4) Prevents cosmetic defects after laminectomy.
5) Easy to apply after a laminectomy or posterior spinal fusion, especially for patients who have a fusion.
6) Provides long term durability, and facilitates repeated surgeries of the spine.

SUMMARY OF THE INVENTION

In one aspect, the present invention provides a surgical kit. The kit can include a shield for covering a portion of the spine of a subject. The shield can include an attachment portion adapted to engage a bone fixation assembly which is adapted to be fixated on multiple vertebra bones of the subject.

In one embodiment, the bone fixation assembly comprises at least one vertebra joining member secured between two bone anchors, each bone anchor comprising a fastener portion adapted to be implanted into a vertebra bone and a head coupling portion adapted to secure the vertebra joining member.

In another embodiment, the attachment portion of the shield is adapted to engage the vertebra joining member of the bone fixation assembly. In alternative embodiments, the attachment portion of the shield is adapted to engage at least one of the bone anchors of the bone fixation assembly.

Alternatively, the attachment portion of the shield includes a hook portion for engaging the vertebra joining members of the bone fixation assembly. The bone fixation assembly may comprise a bone screw or more than one bone screw connected by a vertebral joining member. The vertebral joining member may be a rod, which may have a telescoping configuration.

In some embodiments, the shield has an adjustable transverse width. In one embodiment, the shield includes two parts each containing one hook for engaging a vertebra joining member of the bone fixation assembly, where the two parts are adapted to engage each other at multiple lateral positions. In one embodiment, there are two hooks which are configured to removably attach to the rod, and a connecting member is disposed between the two hooks.

The connecting member may comprise two connecting members slidably joined at a center screw.

The shield may have a vertical length to cover at least two or more vertebrae. The shield may also comprise a plurality of shields, where adjacent shields are stacked in a continuous manner one on top of the other.

The shield may be included in a surgical kit that includes at least one coupling element adapted to secure the attachment portion of the shield to one of the bone anchors. The surgical kit may further include at least one coupling element adapted to secure the attachment portion of the shield to the vertebra joining member. In these embodiments, the coupling element may be a clip having an open end. In one embodiment, the clip may have an omega type shape. The coupling element may be removably attached to a bone screw. In some embodiments, the attachment portion comprises a coupling element comprising two side hooks and a connecting member.

In yet another embodiment, the bone fixation assembly comprises at least two vertebral joining members each secured between two bone anchors. The surgical kit further includes a link adapted to engage each of the two vertebra joining members. The link may include a securing element to secure the shield thereon. In one embodiment, the link can include two connecting members in a slidable configuration with each other so as to allow adjustment of a transverse length of the link across the vertebra. In one embodiment, the shield includes two parts each affixed to a respective member of the two connecting members of the link, and a lateral distance between the two parts can be adjustable as the two connecting members of the link are moved relative to each other.

The attachment portion of the shield can include at least one hole. The shield can include an elongated concavity. The attachment portion can include two parts extending laterally on opposite sides of the shield.

In one embodiment, the shield comprises two lateral parts, each lateral part comprises a shield portion and a hook portion, the shield is fixed to a bone fixation assembly by an attachment portion, and the attachment portion is configured to removably attach to the bone fixation assembly.

In one embodiment, the shield comprises two half-domes, where each half-dome is fixed to one connecting member.

The shield can include or is made from a polymeric material, such as PEEK. In other embodiments, the shield may include a metallic or metal alloy material, such as titanium or its alloys.

The shield can further include at least one therapeutic agent such as an anti-stenotic agent, an anti-fibrotic agent or an antibiotic agent.

BRIEF DESCRIPTION OF THE DRAWINGS

FIG. 2A is a perspective view of a spine protection shield of an embodiment of the present invention; FIG. 2B is a top view of the spine protection shield shown in FIG. 2A;

FIG. 2C is a top view of a spine protection shield of another embodiment of the present invention; FIGS. 2D and 2E are top views of spine protection shields having different attachment portions according to embodiments of the present invention.

FIGS. 10A and 10B depict a mechanism of attachment of the invention to the vertebral column.

DETAILED DESCRIPTION

Figure 1A:
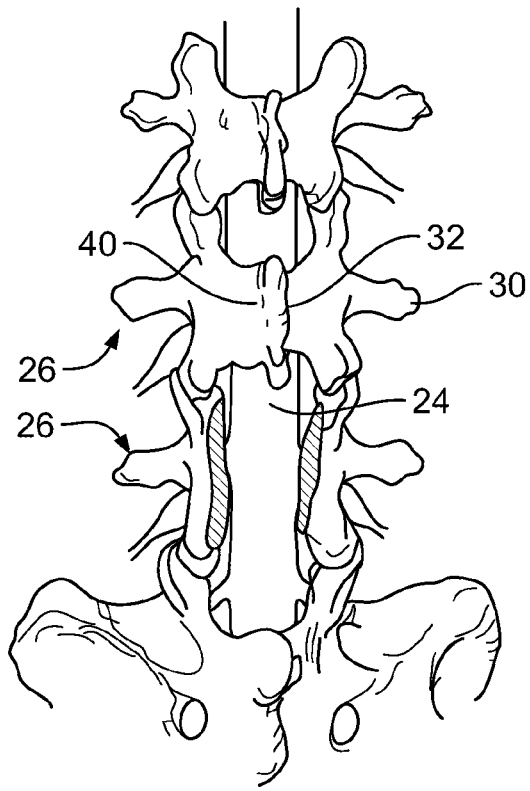
FIG. 1A (prior art) is a partial perspective view of a lumbar vertebrae showing a body dissection associated with a laminectomy.
Figure 1B:
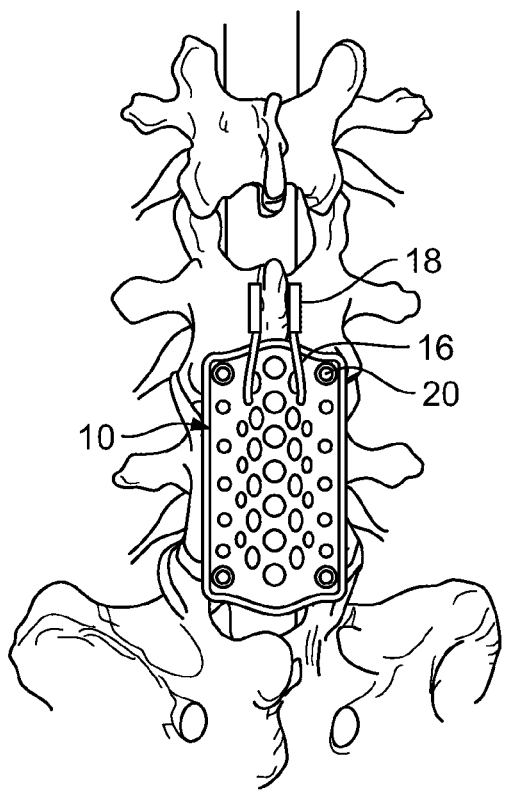
FIG. 1B (prior art) is a partial perspective view showing use of a prior art shield to cover the laminectomy dissection shown in FIG. 1A.

The present invention generally relates to a surgical kit which includes a shield adapted to cover a portion of the spine of a subject, e.g., after laminectomy or after a posterior spinal fusion. The shield includes an attachment portion adapted to engage a bone fixation assembly which is adapted to be fixated on multiple vertebra bone of the subject. The attachment portion can removably attach to the bone fixation assembly.

An example of the shield is shown in FIGS. 2A and 2B. The shield 100 can include a body portion 100, which can take an arcuate shape, 110 (e.g., curved, elliptical or trapezoidal in shape) or have an elongated concavity, as well as attachment portions 120a and 120b, which may include holes or openings 122a and 122b to accommodate attachment pins or other coupling mechanism for fixation of the shield onto bone (i.e., vertebra). The hole can assume a circular, elliptical, square or other shape. Although the attachment portions 120a and 120b are shown to each include two holes; fewer or more holes can be included to provide alternative choices for fixation (an example of the shield having only one hole on each attachment portion is shown in FIG. 2C), e.g., 3, 4, 5, 6, 7, 8, 9, 10 . . . n. The shield 100 may be symmetrical with respect to an axis 101, where the attachment portions extend laterally on opposing sides with respect to the axis 101. In use, the axis 101 can be aligned with the spine in a vertical, axial path. The shield 100 has a length L along the axis (or vertical length) which can be configured to cover one vertebrae, or two, or more consecutive vertebrae of different sections (e.g., cervical, thoracic, lumbar, etc.) of the spine or spinal column, as desired or needed, e.g., 3, 4, 5, 6, 7, 8, 9, 10, vertebra. The shield 100 has a total width W and the body of the shield has a width of W1, both of which can be selected or tailored to suite the location of the shield on the spine where the shield is to be implanted. As shown below, in certain embodiments, the width W and/or W1 can be adjustable.

Alternatively, the attachment portions can have no holes, but instead include other structural features that help secure the shield onto the bone fixation assembly. The means for securing the shield to the bone fixation assembly is described further below. There can also be multiple attachment portions on either lateral side of the shield 100, and the attachment portions can take various shapes and sizes, as illustrated in FIG. 2D (120*a*, 120*b*, 120*a'*, 120*b'*) and FIG. 2E (120*c*, 120*d*).

Figure 3:
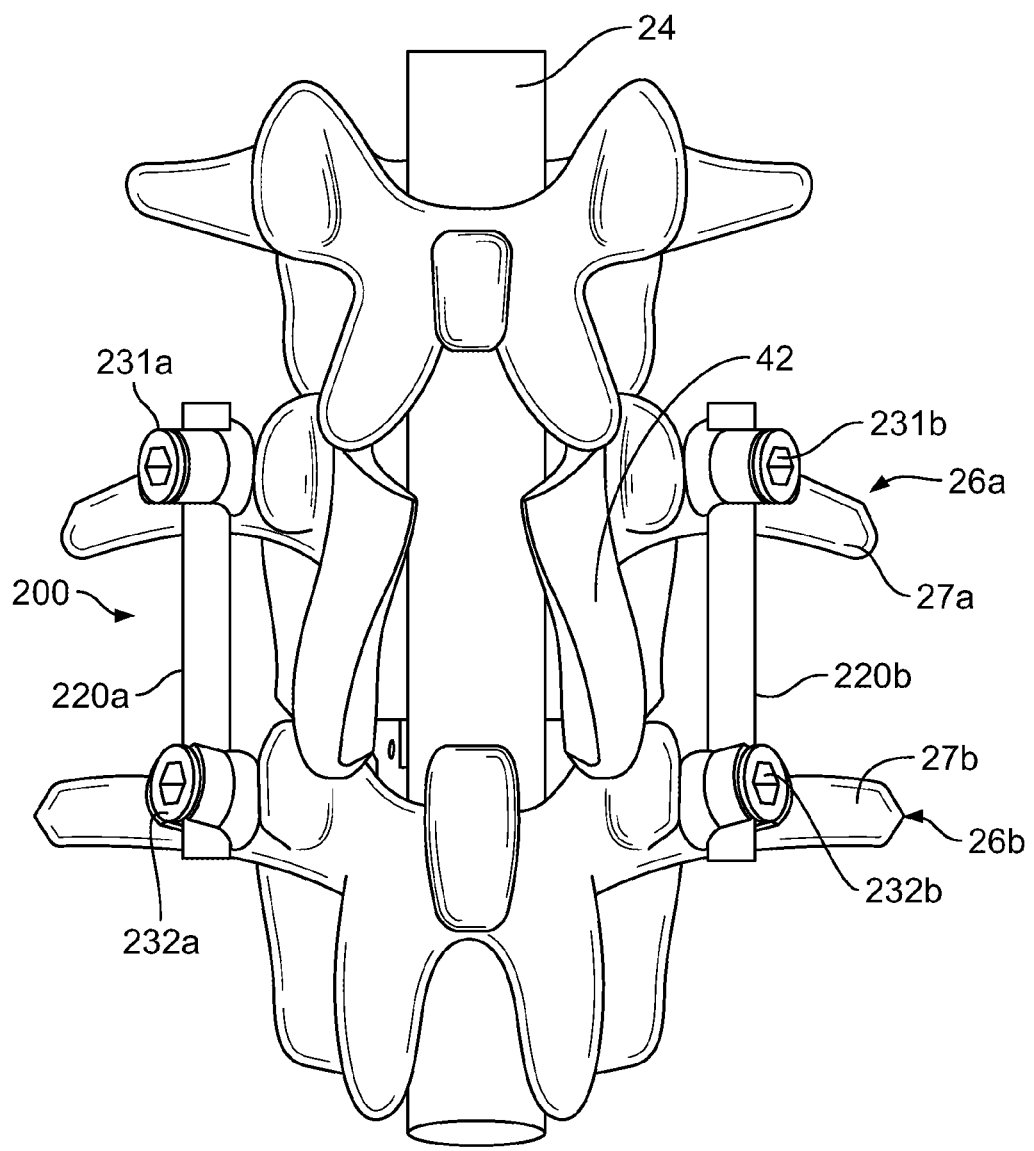
FIG. 3 depicts a bone fixation assembly as implanted on vertebra bones of a portion of the spine of a subject where a laminectomy has been performed.

As described herein, the protection shield is configured to engage a bone fixation assembly, which can be part of the surgical kit, or provided separately. In one embodiment, and as illustrated in FIG. 3, a bone fixation assembly 200 can include a vertebra joining member 220*a* secured between two bone anchors 231*a* and 232*b*, and a vertebra joining member 220*b* secured between two bone anchors 232*a* and 232*b*. The bone anchors can be implanted into a portion of the transverse process 27*a* and 27*b* of the respective vertebra 26*a* and 26*b*. The vertebra joining member 220*a*/220*b* between the anchors 231*a*-232*a* and between the anchors 231*b*-232*b* help inhibit the relative motion between the two vertebra 26*a* and 26*b*. While shown as being cylindrical, the vertebra joining member 220*a*/220*b* can have any desired cross section shapes, such as elliptical, rectangular or other multilateral shapes. Also shown in FIG. 3 is a cut lamina 42 (the spinal process and part of the lamina have been removed) from which a portion of the spinal cord 24 is exposed. The shield of the present invention, which when in use, can cover (without touching) this portion of the exposed spinal cord 24 and can attach to the bone fixation assembly 200. For a simple laminectomy without spinal fusion, a protection shield 100 shown in FIG. 2 can also be simply fixated on the remaining bone (or residual lamina) or medial facet joint using cortical screws which are inserted through the holes 122*a* and/or 122*b*.

Figure 4:
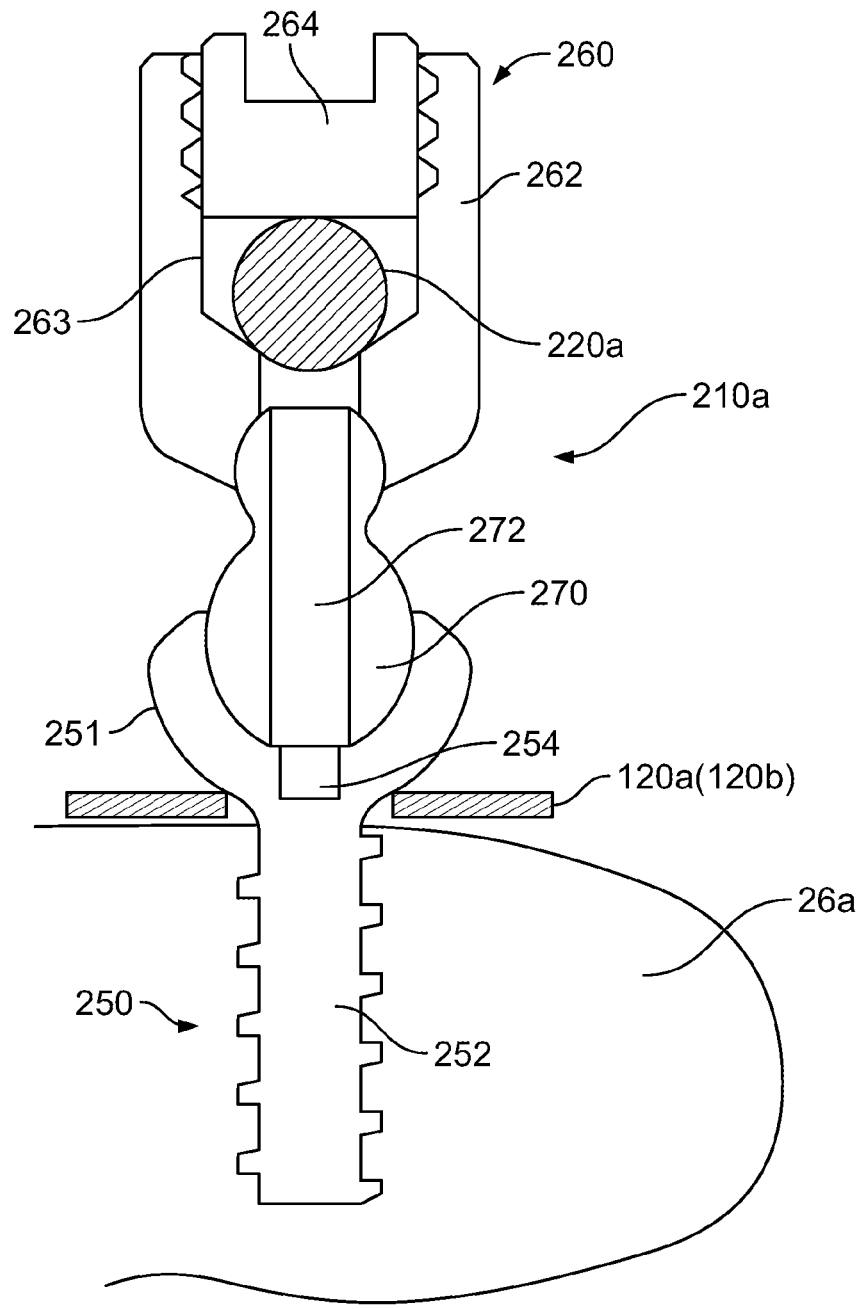
FIG. 4 depicts an exemplary internal structure of an anchor of a bone fixation assembly.

The bone fixation assembly illustrated in FIG. 3 can take various configurations. For example, FIG. 4 depicts an illustrative cross section view of an embodiment of the bone fixation assembly shown in FIG. 3. The anchor 210*a* includes a fastener portion 250, which may be a bone screw having a head portion 251 and a threaded portion 252 for facilitating its implantation into vertebra bone (e.g., a transverse process portion of the vertebra 26*a* shown in FIG. 3). The fastener portion 250 includes a receptacle 254 which can be used to drive the threaded portion into the bone, e.g., by a screw driver or other mechanical device. The anchor 210*a* further includes a head coupling portion 260, which includes a housing 262 and a locking member 264 which can be configured to engage with an inner surface 263 of the housing 262 with mating threads, and lock the vertebra joining member 220*a* into place by friction. In one embodiment, the bone fixation assembly comprises two bone screws which are connected by a vertebral joining member. The vertebra joining member may be removably attached to the one or more bone screws.

In the embodiments shown in FIGS. 3 and 4, when the locking member 264 is in the unlocked position (e.g., when it is not contacting the vertebra joining member 220*a*), the vertebra joining member 220*a* can be moved along its length direction, allowing adjustment of the length of the vertebra joining member 220*a* disposed between the two anchors 231*a* and 232*a* (and between the two anchors 231*b* and 232*b*). The vertebra joining member can be a rod. Alternatively, the vertebra joining members can have a telescoping configuration along its long axis; this telescoping configuration allows adjustment of the lengths of the vertebra joining member 220*a* disposed between the two anchors 231*a* and 232*a* after two ends of the vertebra joining member 220*a* have been locked onto the respective anchors.

Additionally, the anchor 210*a* may include a link 270 connecting the head coupling portion 260 and the fastener portion 250 with a double ball and socket joint configuration which allows for rotation and/or pivoting of the head coupling portion 260 relative to the axis of the fastener portion 250. A passage 272 is defined within the link 270, which is aligned with the receptacle 254 of the fastener portion 250, to allow a tightening tool, e.g., a screw driver, to directly contact the receptacle 254 through the head coupling portion 260 (before the vertebrae joining member 220*a* is installed) to secure the fastener portion 250 into the bone.

The shield of the present invention can engage the bone fixation assembly in various ways. For example, the attachment portion of the shield can be fixed onto the vertebra bone by the fastener portion 250 as shown in FIG. 3, e.g., by inserting the threaded portion 252 through a hole of the attachment portion, thereby allowing the head portion 251 to secure the attachment portion 120*a* or 120*b* of the shield onto the vertebra bone.

Figure 5:
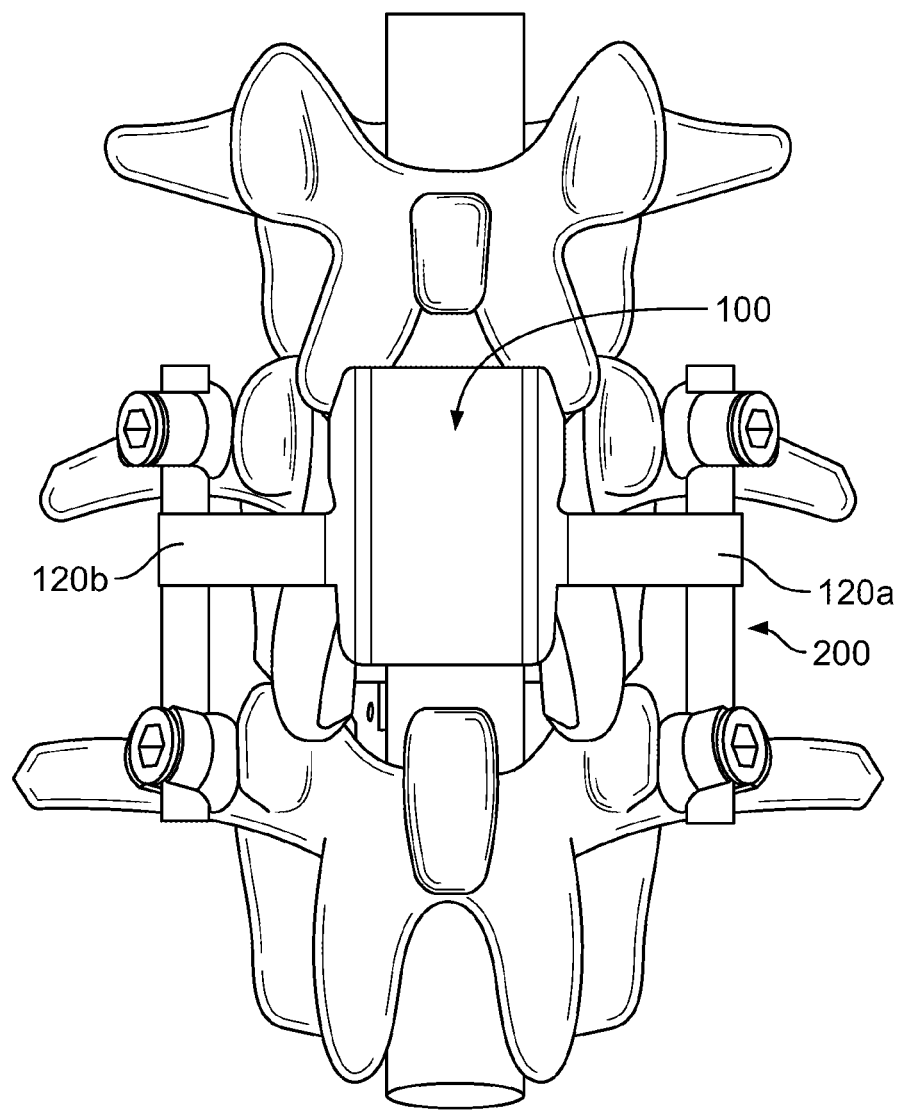
FIG. 5 depicts a spine protection shield installed on a laminectomy site via a bone fixation assembly according to certain embodiments of the present invention.

In a preferred embodiment, the shield is secured on the bone fixation assembly after the bone fixation assembly has already been implanted. As illustrated in FIG. 5, the shield 100 can be secured to the rods of the bone fixation assembly (which has already been installed on bone) via the attachment portions 120*a*/120*b*. This approach allows easy installation and rapid as well as replacement of the shield while keeping the fixation assembly in place.

To facilitate securement of the shield onto the bone fixation assembly, the protection shield can include an attachment portion (s) that is shaped and configured to directly engage the bone fixation assembly (e.g., on the rods or on the bone anchors). Alternatively, the surgical kit can include one or more coupling elements to couple an attachment portion of the shield to the bone fixation assembly, e.g., to the vertebra joining member, and/or to the head coupling portion(s) of the bone fixation assembly 200. Preferably, the coupling element is secured on the vertebra joining member 220 at a position between the two bone anchors associated with the vertebra joining member.

Figure 6A:
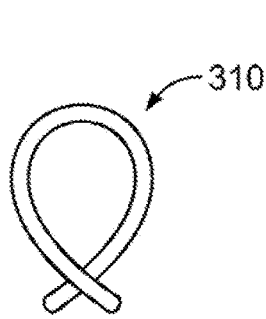
FIGS. 6A-6M depict various configuration of a coupling element for securing a spine protection shield onto a vertebra joining member of a bone fixation assembly, according to embodiments of the present invention.
Figure 6B:
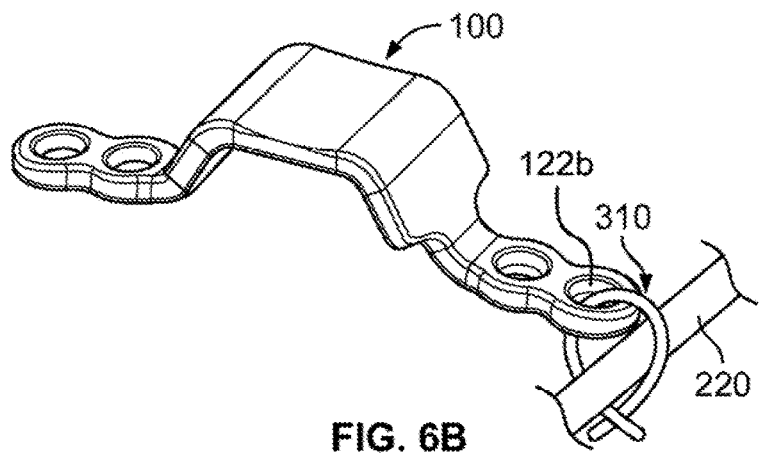

As illustrated in FIG. 6A, a coupling element to secure the attachment of the vertebra joining member can take a form of a clip 310. The clip can be configured with appropriate elasticity and contour length to wrap around at least a portion of the circumference of the vertebra joining member of the bone fixation assembly so as to secure the attachment portion against the vertebra joining member 220. FIG. 6B illustrates a shield 100 being secured to the vertebra joining member 220 by inserting the clip 310 through a hole 122*b* of an attachment portion of the shield 100 and wrapping around a circumference of the vertebra joining member 220.

Figure 6C:
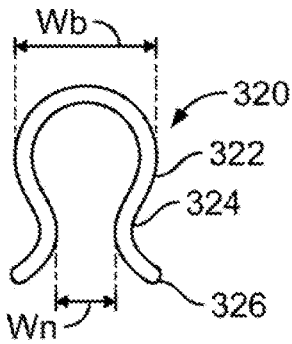
Figure 6D:
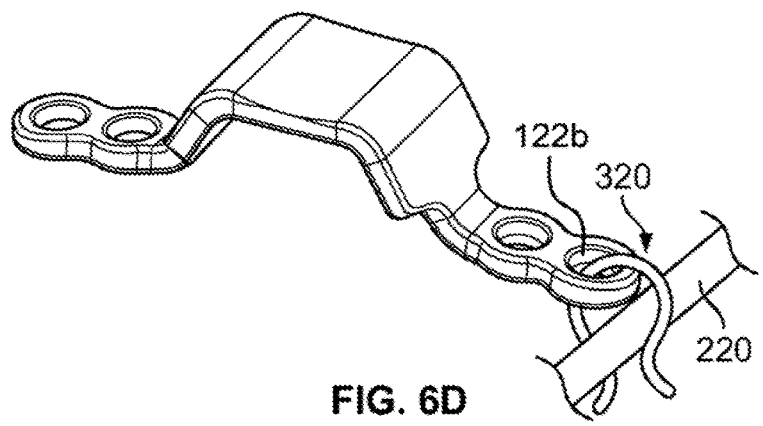

As illustrated in FIG. 6C, the coupling element can also take a form of a clip 320 having an open end, or an omega ("Ω") shape, which includes a bulbous portion 322 having an opening width of Wb, a neck portion 324 having an opening width Wn (Wn<Wb), and a flared end portion 326. FIG. 6D illustrates a shield 100 being secured to the vertebra joining member 220 by inserting the clip 320 through a hole 122 of an attachment portion of the shield 100 and wrapping it around a circumference of the vertebra joining member 220. Preferably, the size, configuration, and elasticity of the omega ("Ω") shape shaped clip 320 are such that the bulbous portion 322 can wrap around at least more than 180° of the circumference of the vertebra joining member 220, and that the width Wn of the neck portion 324 when the clip 320 is secured on the vertebra joining member 220 is smaller than the diameter of the vertebra joining member 220. The advantage of the omega ("Ω") shape configuration includes easy deployment of the clip 320. An operator can push the open end toward the vertebra joining member 220, and the open end would be expanded due to the elasticity of the clip 320, thereby allowing the bulbous portion 322 to snap-fit on the circumference of vertebra joining member 220, with the aid of the neck portion 324 to lock the vertebra joining member 220 into place by friction.

Figure 6E:
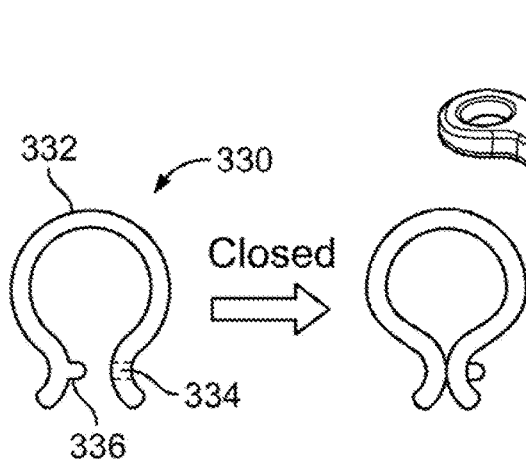
Figure 6F:
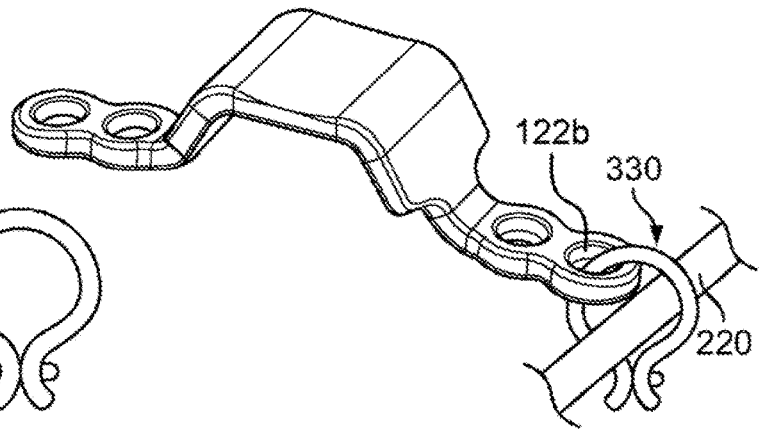

As illustrated in FIG. 6E, the coupling element can also take a form of a clip 330 having a locking mechanism near the ends of the clip. Clip 330 includes an elongate member 332, a protruded portion 336 near one end of the elongate member 332, and a port 334 near the other end of the elongate member 332. The protruded portion 336 is configured with appropriate dimension to be inserted into the port 334 to form a closed structure where the protrusion 336 frictionally engages the port 334. The closed structure can be reopened manually if needed, but otherwise has sufficient stability to be implanted into the body for long term use. The contour length of the elongate member 332 between the protruded portion 336 and the port 334 can be tailored to be sufficient to wrap around the circumference of the vertebra joining member to allow the insertion of protruded portion 336 into the port 334. FIG. 6F illustrates a shield 100 being secured to the vertebra joining member 220 by inserting the elongate member 332 of a clip 330 through a hole 122b of an attachment portion of the shield 100 and wrapping it around a circumference of the vertebra joining member 220, and the protruded portion 336 is locked in the port 334 to form a closed structure to secure the shield onto the vertebra joining member 220.

Figure 6G:
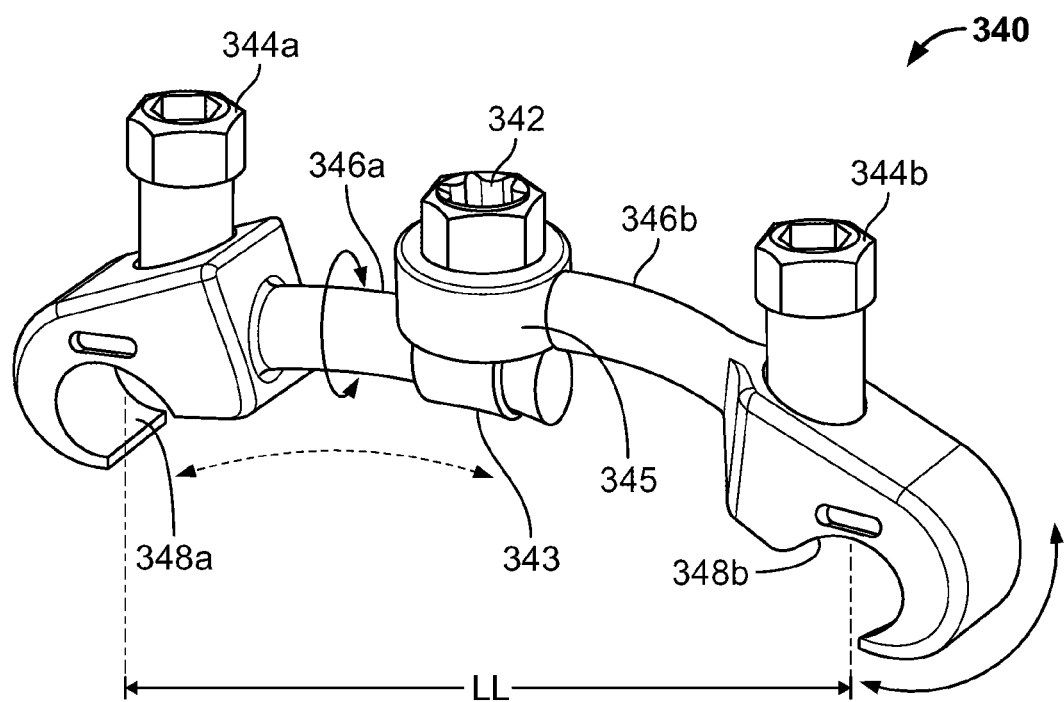
Figure 6H:
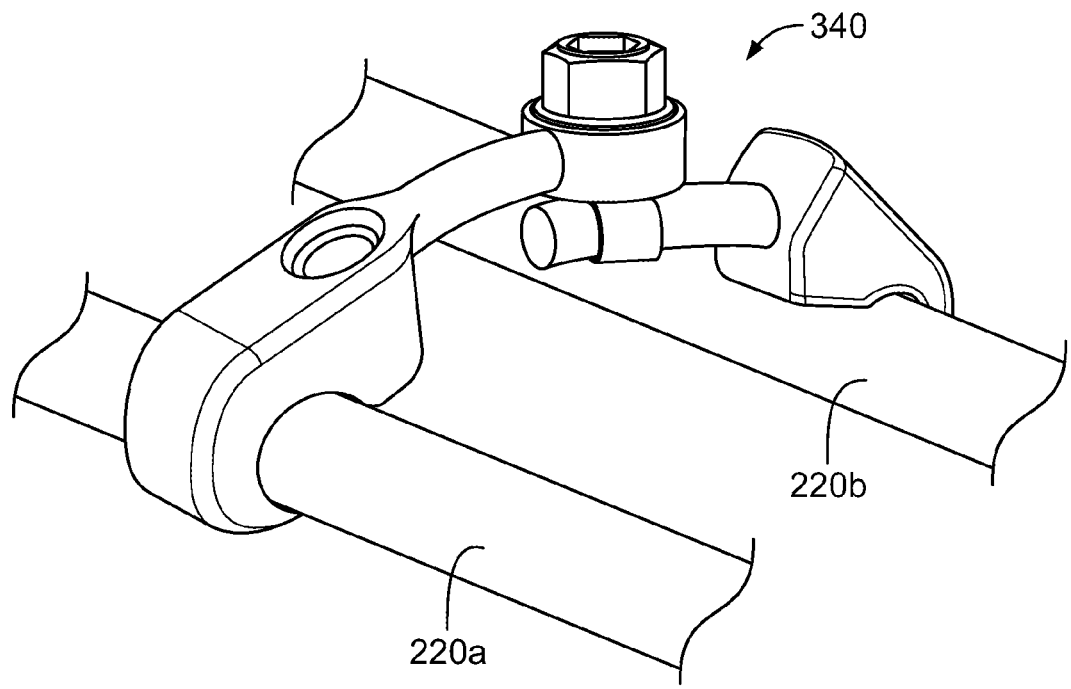

In another embodiment, as illustrated in FIGS. 6G and 6H, the coupling element can take the form of a link 340 that is configured to span transversely over the vertebra to engage the vertebra joining members (rods) of the bone affixation assembly installed on both sides of the spine (see FIG. 3). The link 340 includes lateral or side hooks 348a and 348b dimensioned and configured to engage the vertebra joining members (rods). Each hook also is equipped with screws 344a/344b for tightening against the respective rod. A connecting member 346b extends from hook 348b. The distal end of the connecting member 346b includes an enlarged portion 345 for receiving a center screw 342, and a hoop structure 343 for slidably receiving a connecting member 346a extending from the hooks 348a/348b. The transverse length LL between the hooks 348a and 348b is adjustable by virtue of a slidable connection between the two connecting members 346a and 346b. The connecting member 346a can rotate within the hoop 343, and the two connecting members 346a and 346b can also deviate from a linear arrangement (e.g., they can form an angle), thereby permitting the link 340 to couple with the vertebra joining members of the bone fixation assembly that might not be parallel configuration. In operation, when desired length LL and other adjustable parameters of the configuration of the link 340 are obtained (e.g., when a tight fit between the hooks and vertebra joining member are obtained), the center screw 342 can be tightened to engage connecting member 346a thereby fixing the length LL. The screws 344a and 344b can be tightened so that they securely engage the vertebra joining member (rods) of the bone fixation assembly. FIG. 6H shows the coupling element 340 as secured on the vertebra joining members 220a/220b of the bone fixation assembly.

Figure 6I:
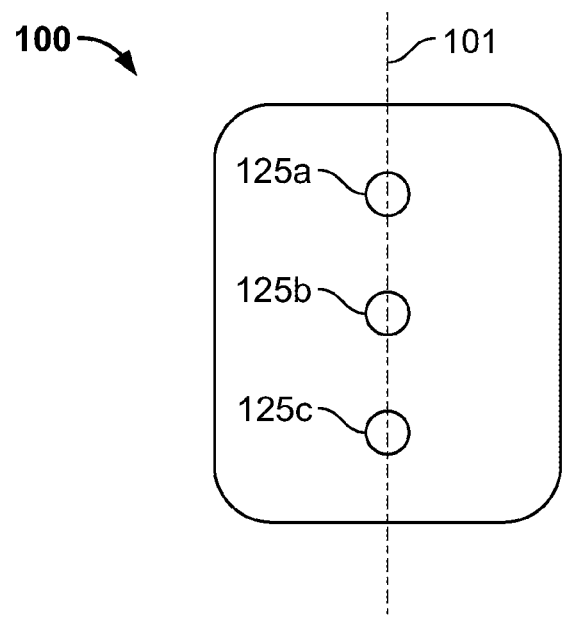
Figure 6J:
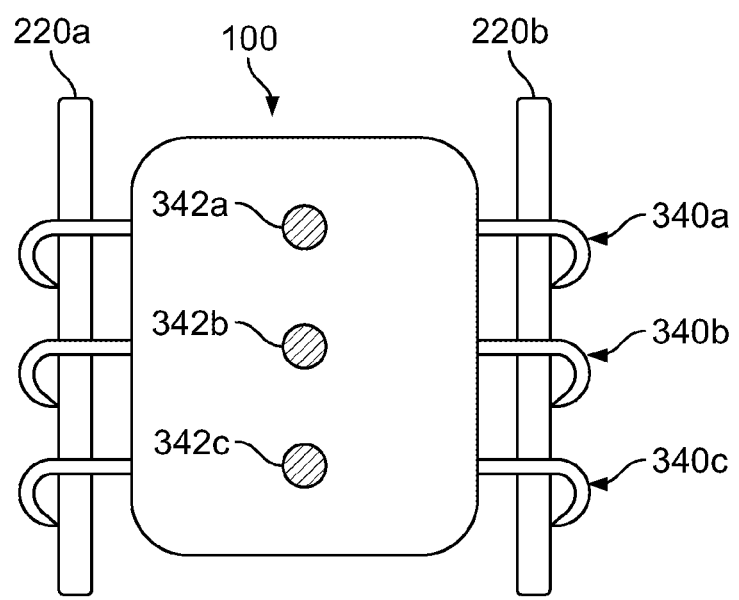

The shield of the present invention can be secured in various ways. For example, as schematically illustrated in FIG. 6I, the shield 100 can have multiple apertures 125a, 125b, and 125c positioned along its long or vertical axis, e.g., along the longitudinal axis 101 of shield 100, where the size of the apertures is adapted such that screw 342 of the link 340 can be inserted through the apertures to secure the shield 100 thereon. As illustrated in FIG. 6J (a top down view of the shield 100 assembled on three links), shield 100 is secured by three links 340a, 340b, and 340c via center screws 342a, 342b, and 342c of the links (the three links 340a, 340b, and 340c are secured to the respective rods 220a and 220b by their respective side hooks). Thus, when the center screws 342a, 342b, and 342c are tightened, the lateral span of the links 340a, 340b, and 340c is fixed, and the shield 100 is secured to the vertebra at the same time.

Figure 6K:
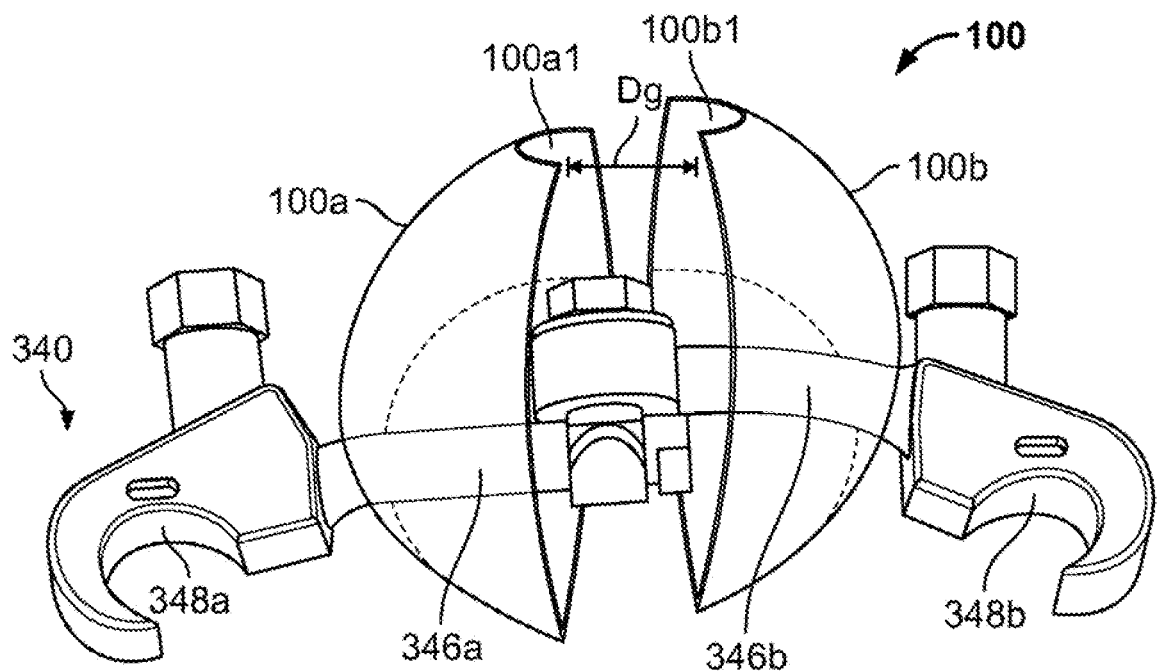
Figure 6L:
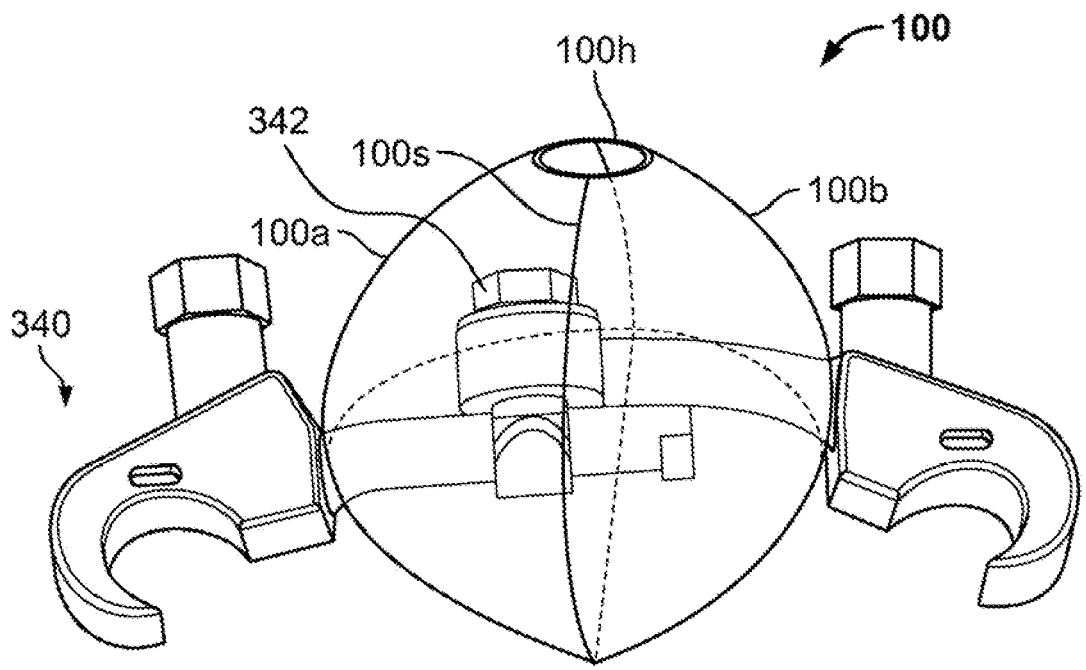

FIGS. 6K and 6L illustrate an alternative example where the coupling element takes the form of a link 340 as previously described in connection with FIGS. 6G and 6H. In this embodiment, a shield 100 can include two parts 100a and 100b, which assume a configuration of a half-dome or curved shell with a cut top 100a1 and 100b1, respectively. Parts 100a and 100b can be fixed on the connecting members 346a and 346b of the link 340, respectively. The fixation can be accomplished by mechanical coupling, chemical bonding, physical bonding, etc. The lateral distance between the two parts 100a and 100b of the shield can be adjusted by sliding the connecting member 346a relative to the connecting member 346b. For example, when the two lateral hooks 348a and 348b are in a first, open configuration, as shown in FIG. 6K, there is a lateral gap Dg between the two parts 100a and 100b of the shield. After the two connecting members 346a and 346b are slid against each other such that the two lateral hooks 348a and 348b are in a second, more compact configuration, as shown in FIG. 6L, the two parts 100a and 100b meet in a center seam 100s or at least partially overlap in the middle such that there is no longer a lateral gap between the two parts 100a and 100b. In this configuration, the upper portion of the shield 100 can mimic the shape of a spinous process. This configuration can also be used as a final assembled configuration for implantation, at which the connecting members 346a and 346b can be locked against each other by tightening the screw 342 by a tightening tool (e.g., a screw driver) which can access the screw 342 via the top opening 100h formed by the two parts 100a and 100b at this configuration.

In the above embodiments where a coupling element is used to couple the shield onto the vertebra joining member, for improved friction between the coupling element and the vertebra joining member, the vertebra joining member can include grooves, dents, dimples, or other surface irregularities.

Figure 6M:
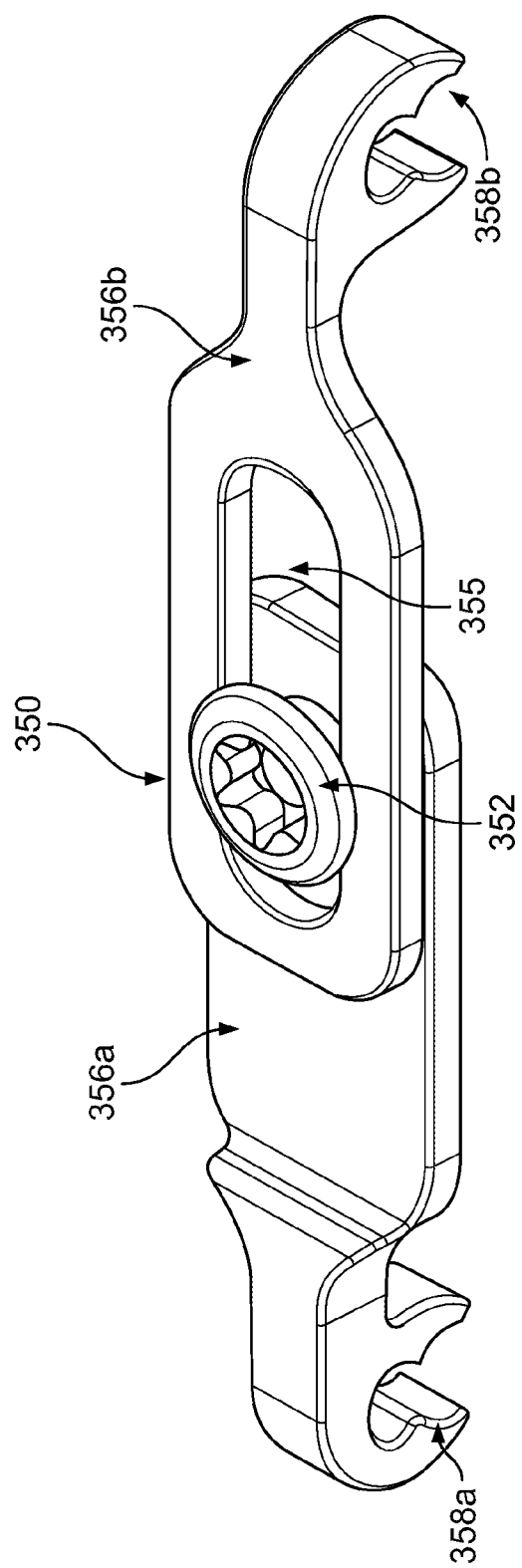

In another embodiment, illustrated in FIG. 6M, the coupling element takes the form of a link 350 that is configured to span transversely over the spine to engage the vertebra joining members (rods) of the bone fixation assembly which are installed on both sides of the spine. The link 350 includes lateral or side hooks 358a and 358b dimensioned and configured to engage the vertebra joining members (rods). The hook has an open end which can be in the form of an "Ω" (omega) shape. A connecting member 356b extends from hook 358b; a connecting member 356a extends from hook 358a. The distal end of the connecting member 356b includes an elongated port 355 for receiving a bolt 352 which is attached to connecting member 356a; the bolt extends upward through the port 355 to slidably connect connecting members 356a and 356b. The transverse length LL between the hooks 358a and 358b is adjustable due to the slidable connection between connecting members 356a and 356b. The connecting members 356a and 356b can rotate with respect to each other to form a non-linear arrangement. For example, the connecting members can move to form an angle between them which is less than 180°. Bolt 352 can be tightened to engage connecting member 356a with connecting member 356b, thereby fixing the length LL.

Figure 7B:
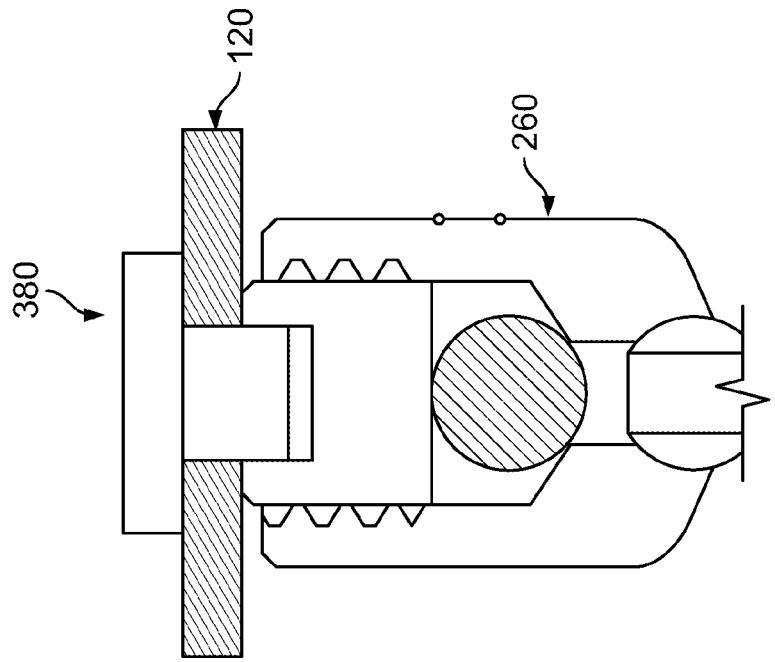
FIGS. 7A and 7B depict coupling a spine protection shield with an anchor of a bone fixation assembly, according to embodiments of the present invention.
Figure 7A:
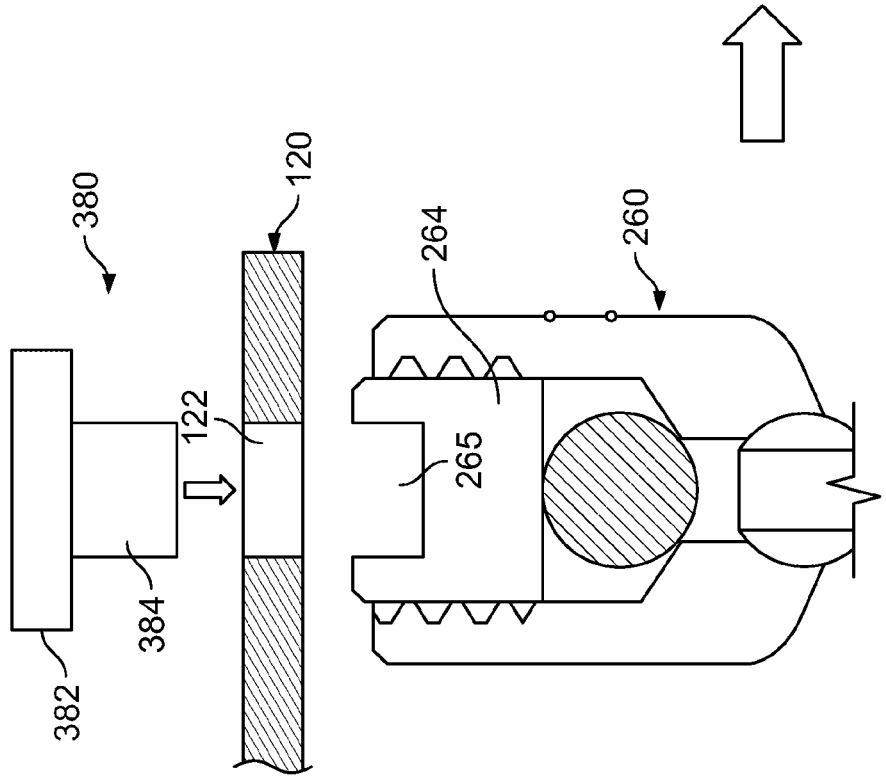

In other embodiments, the coupling element can be configured for coupling the attachment portion of the shield 100 directly with the bone anchors of the bone fixation assembly. As another example, these clips can be used to couple to the head coupling portion 260 as shown in FIG. 4. Other forms of coupling elements can also be used. For example, FIGS. 7A and 7B show an attachment pin (or stud/screw) 380 having a head portion 382, an engaging portion 384 dimensioned and configured to be inserted into the socket 265 of the locking member 264 of the head coupling portion 260 (see FIG. 4) through a hole 122a/122b of an attachment portion 120a, 120b of a shield, thereby securing the attachment portion 120a, 120b of the shield onto the head coupling portion 260.

Figure 8A:
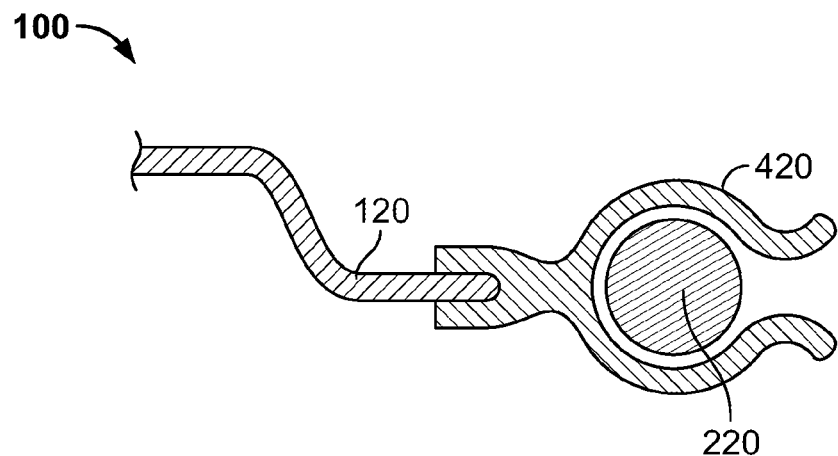
FIGS. 8A-8I depict various configurations of an attachment portion of a spine protection shield that includes structural features for engaging a portion of a bone fixation assembly, according to embodiments of the present invention.
Figure 8B:
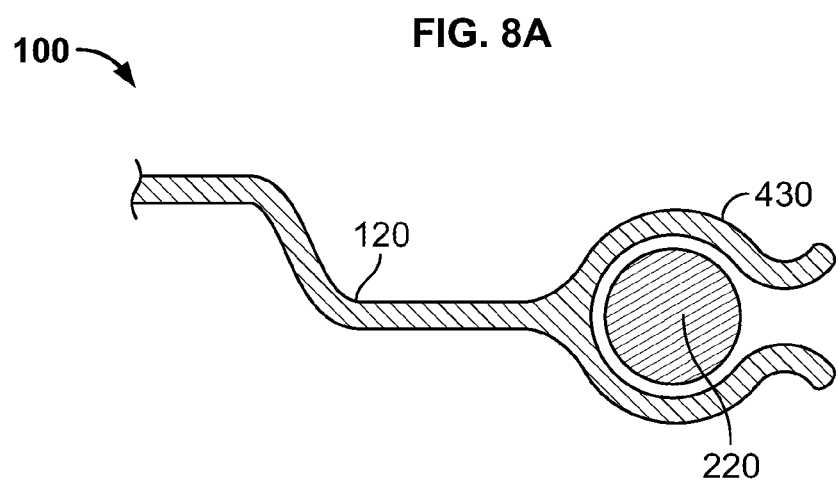

In further embodiments, an attachment portion of the shield of the present invention can include an integral portion which is configured to engage the bone fixation assembly. For example, the various coupling elements (clips) as shown in FIGS. 6A, 6C, and 6F can be fabricated as part of an attachment portion of the shield 100, or integrated with an attachment portion of the shield 100. As illustrated in FIG. 8A, an omega ("Ω") shape shaped clip 420 can be manufactured separately from the shield 100 and then integrated or joined with an attachment portion 120 of the shield 100 (e.g., by welding, adhering, or other commonly known techniques in the art). FIG. 8B illustrates a shield 100 having an attachment portion 120 which includes an omega ("Ω") shape shaped end portion 430. The clip 420 or omega ("Ω") shape shaped end portion 430 can be used for engaging a vertebra joining member 220, or a bone anchor associated with a vertebra joining member 220. While the open end of the clip 420 or omega ("Ω") shape shaped end portion 430 is shown in FIGS. 8A and 8B as being oriented laterally toward the vertebra joining member 220, other orientations are also contemplated, for example, downward, or obliquely downward.

Figure 8C:
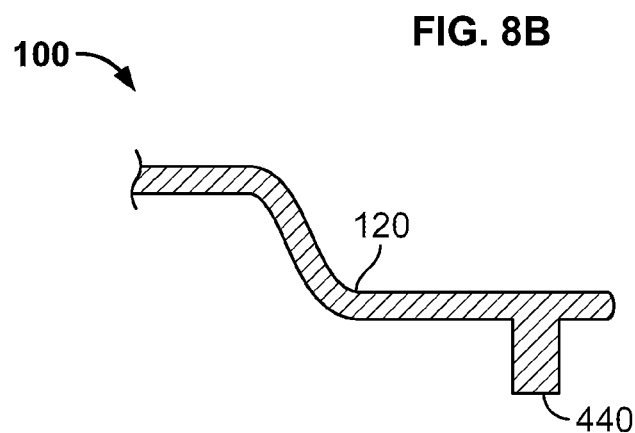

An attachment portion of the shield of the present invention can also include other integral structural element configured to engage a part of the bone fixation assembly other than the vertebra joining member(s). For example, as illustrated in FIG. 8C, the attachment portion 120 of a shield 100 includes a protruded portion 440 which is dimensioned and configured, such as the attachment pin 380 in FIGS. 7A and 7B, to be inserted into the socket 265 of the locking member 264 of the head coupling portion 260, thereby securing the attachment portion 120 of the shield 100 onto the head coupling portion 260.

Figure 8D:
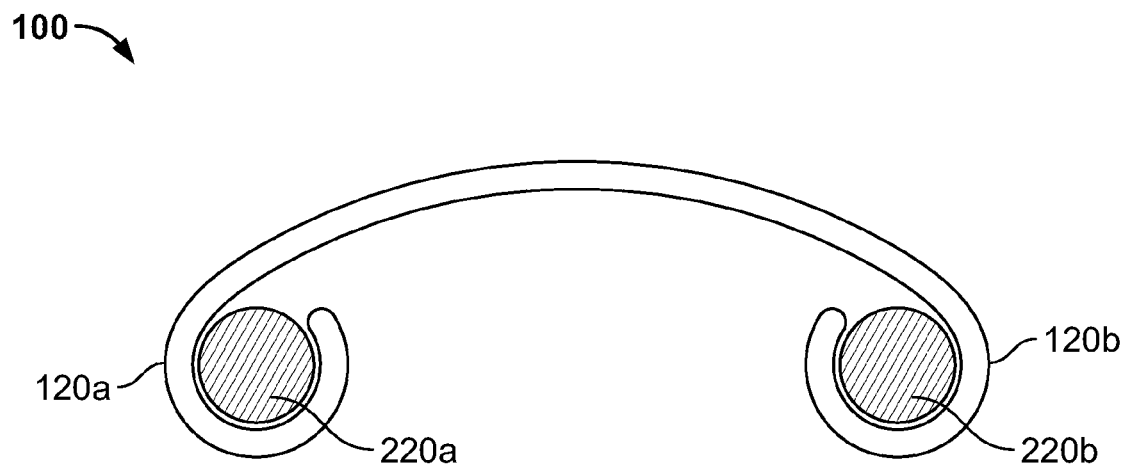
Figure 8E:
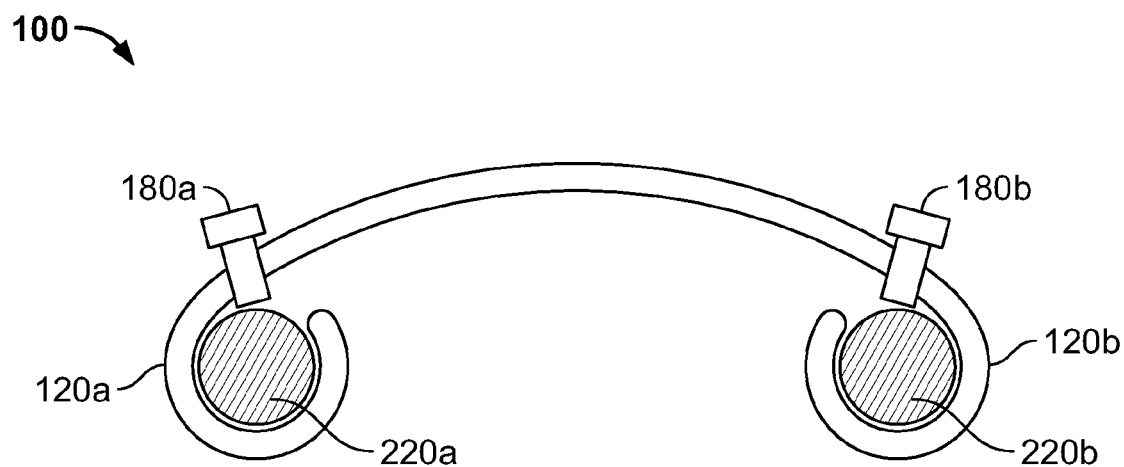

FIG. 8D illustrates another example of attachment portions 120a and 120b of shield 100 configured as hooks to engage vertebra joining members 220a and 220b on both lateral sides. In this embodiment, the shield 100, the attachment portions 120a/120b are formed from two pieces which are joined together. FIG. 8E illustrates a variation of the structure shown in FIG. 8D, where attachment pins 180a and 180b (e.g., screws) located proximal to the hooks can be fastened to contact the vertebra joining members (rods) 220a and 220b, thereby providing further security for the engagement between the hooks and the vertebra joining members (rods) 220a and 220b.

Figure 8F:
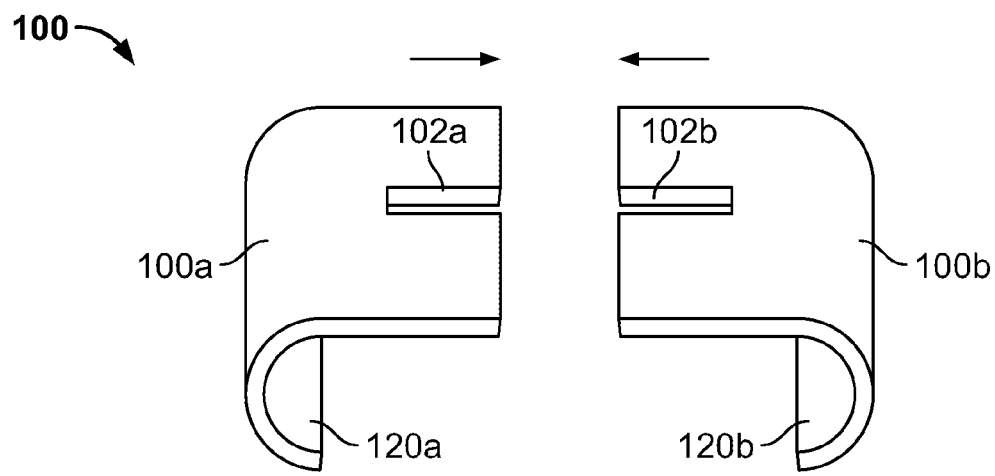
Figure 8G:
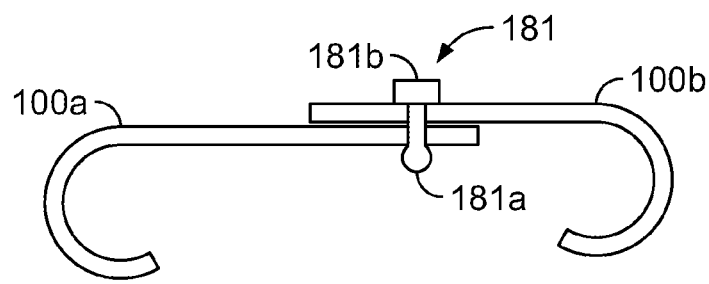
Figure 8H:
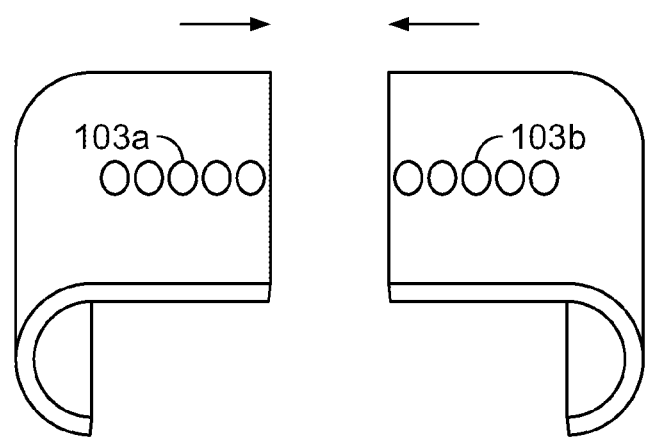

FIGS. 8F-H illustrate a further example of attachment portions 120a and 120b of shield 100 configured as hooks, where the shield 100 has an adjustable transverse or lateral width. In this embodiment, the shield 100 includes two lateral parts (or halves) 100a and 100b, each including a slit 102a and 102b oriented along the width direction. To assemble the shield during surgery, the operator can first engage the two respective hooks with the vertebra joining members of the bone fixation assembly (not shown), and slide the two halves of the shield toward each other until a desired position is reached where the two halves are partially overlapping with each other with the slits 102a/102b aligned. Then the operator can secure the shield at this position (see FIG. 8F) using an attachment pin 181 through the opening of the slits 102a and 102b. The attachment pin 181 can include a bolt 181a and nut 181b. Instead of the slits 102a/102b, a series of holes 103a/103b arranged in the width direction on 100a and 100b can also be employed (see FIG. 8H) to provide discrete stop positions for adjusting the width of the shield to cover the vertebra.

Figure 8I:
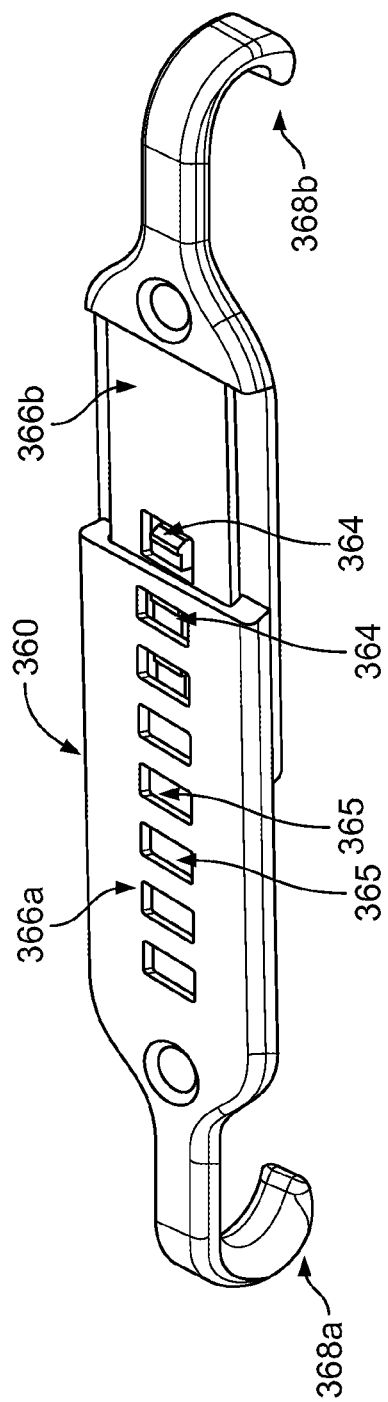

In another embodiment, and as shown in FIG. 8I, the coupling mechanism of the coupling element or link can take the form of a series of protrusions configured to mate with a series of apertures. The coupling element is configured to span transversely over the spine to engage the vertebra joining members (rods) of the bone affixation assembly (not shown). In this case, securement between the two halves of the shield can be accomplished by directly coupling between the protrusions and the apertures. The coupling mechanism 360 includes lateral or side hooks 368a and 368b dimensioned and configured to engage the vertebra joining members (rods). A connecting member 366a extends from hook 368a and a connecting member 366b extends from hook 368b. Connecting member 366b comprises a series of protrusions 364, which may be evenly spaced along its length. Connecting member 366a comprises a series of apertures 365, which may be evenly spaced along its length, and which are configured to mate with the protrusions 364 of connecting member 366b. The protrusions 364 should be flush with the external surface of the apertures 365. The transverse length LL between hooks 368a and 368b is adjustable with respect to the mating, or joining, of the protrusions 364 and the apertures 365, which can adjust such that one or more than one protrusion is mated with one or more than one aperture.

Figure 9B:
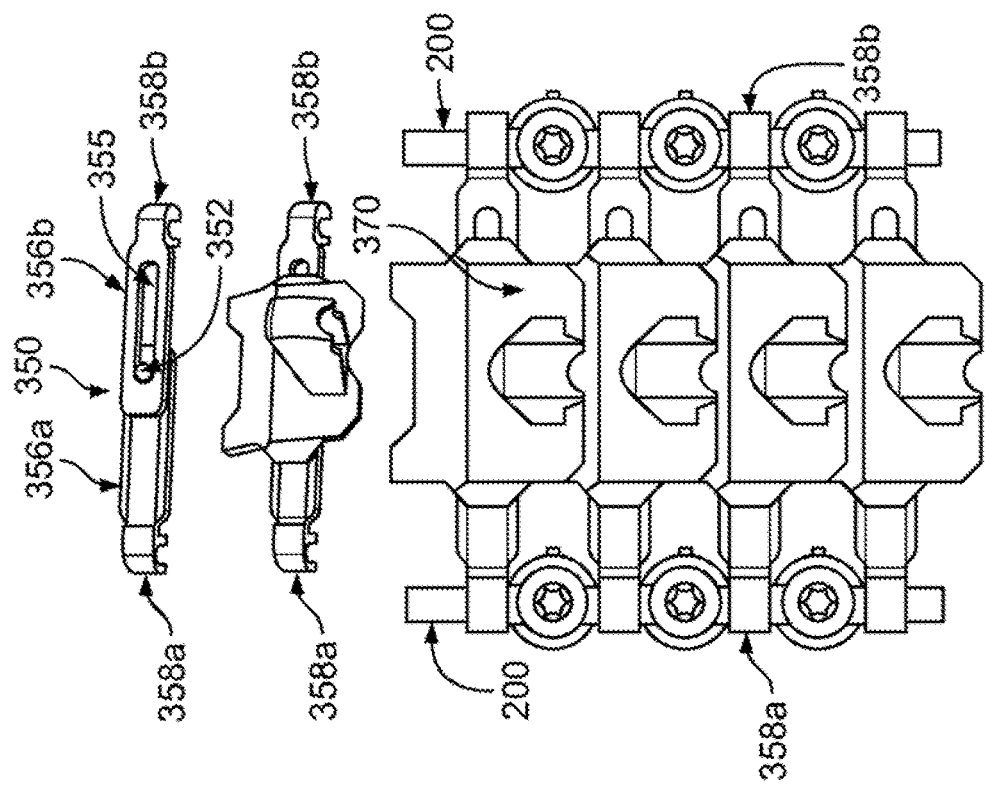
FIGS. 9A and 9B depict an embodiment of the invention.
Figure 9A:
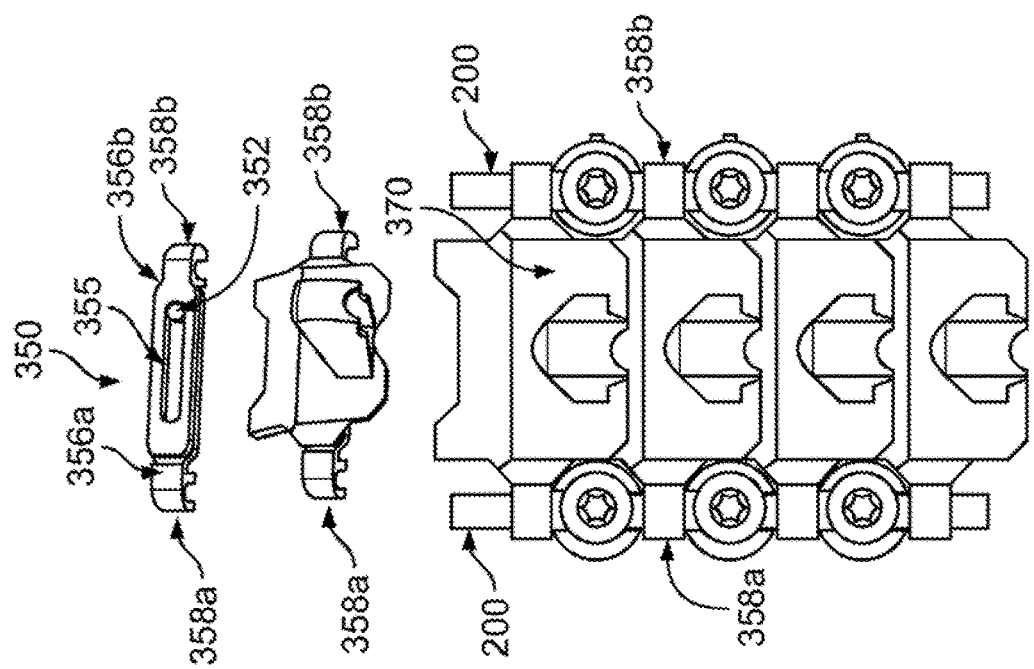

FIGS. 9A and 9B illustrate an embodiment of the coupling element of FIG. 6M attached to a spine. FIG. 9A shows the invention with the coupling element in a closed position while FIG. 9B shows the invention with the coupling element in a open position. As previously described, the coupling element may be in the form of a link 350 configured to span transversely over the vertebra of the spine to engage the vertebral joining members (rods) 200 installed on either side of the spine. The link 350 comprises side hooks 358a and 358b dimensioned and configured to engage the vertebra joining members 200. The link 350 further comprises a connecting member 356b extending from hook 358b and connecting member 356a extending from hook 358a. The distal end of the connecting member 356a comprises a bolt 352 and the distal end of the connecting 356b comprises an elongated port 355 for receiving the bolt 352 to slidably connect the connecting members. The shield 370 can be attached on top of the coupling mechanism. The arrangement of the shield 370 and the vertebral coupling element allows the shields to stack one on top of the other to form a continuous, yet flexible shield along the spinal column.

As illustrated in FIGS. 9A and 9B, the surgical kit may comprise one shield or may comprise more than one shield. For example, the surgical kit may comprise 2, 3, 4, . . . , n shields. When using more than one shield, the shields become stacked one above the other along the spinal column. Each shield is designed to cover one vertebra. If more than one vertebra needs to be covered, then more than one shield would be employed with each shield covering one vertebra.

FIGS. 10A and 10 B illustrate the attachment of the present invention to a bone fixation assembly. In FIG. 10A, an embodiment of the shield 370 is connected to the caudal ridge of the spinous process through the connection of the hooks 358a and 358b to the vertebra joining members (rods) 200. FIG. 10B shows an embodiment of the shield 370 when the distance between the spinous process and the shield is closed and the invention is snapped to the cephalad ridge.

In the various embodiments illustrated above, the bone fixation assembly, the coupling element that couples the bone fixation assembly with the shield, as well as the shield, can be made from various biocompatible materials, such as metal, metal alloys, polymeric materials, including bioabsorbable materials such as polylactic acid, polyglycolic acid, poly-ε-caprolactone, or mixtures or copolymers thereof. Examples of materials that may be used include stainless steel (SST), nickel titanium (NiTi), or polymers. Examples of other metals which may be used include, super elastic NiTi, shape memory NiTi, Ti—Nb, Ni—Ti approx. 55-60 wt. % Ni, Ni—Ti—Hf, Ni—Ti—Pd, Ni—Mn—Ga, 300 to 400 series 304, 316, 402, 440 SST, MP35N, 17-7 PH SST, other spring steel or other high tensile strength material or biocompatible metal material. In one preferred embodiment, the material is super elastic or shape memory NiTi, while in a second preferred embodiment, the preferred material is SST.

Alternatively, the shield may be formed from polymers. Examples of polymers include polyimide, PEEK, nylon, polyurethane, polyethylene terephthalate (PET), latex, HDHMWPE and thermoplastic elastomers.

Depending on the material as well as the structural requirements in terms of flexibility, the wall thickness of the shield at any point can vary, e.g., from about 0.05 mm to 2 mm, e.g., 0.05 mm to about 1 mm, about 0.1 mm, 0.2 mm, 0.3 mm, 0.4 mm, 0.5 mm, 0.6 mm, 0.7 mm, 0.8 mm, 0.9 mm, 1.0 mm, etc. The inner diameter of the shield can vary, e.g., from about 0.1 mm to about 2 mm, or from about 0.25 mm to about 1 mm, e.g., about 0.2 mm, about 0.3 mm, about 0.4 mm, about 0.5 mm, about 0.6 mm, about 0.7 mm, about 0.8 mm, about 0.9 mm, about 1 mm, about 2 mm, about 2.5 mm, about 3 mm thickness.

The spine protection shield 100 can be impregnated or coated with one or more therapeutic or pharmaceutical agents, such anti-restenotic agents, anti-fibrotic agents, or anti-inflammatory agents, antibiotics, or combinations of any of these agents. Such agents can be impregnated in a controlled-release layer which is coated on the protection shield. The controlled release layer can be formed from proteins such as collagen, fibrin, tropoelastin, elastin, crosslinked tropoelastin and extracellular matrix component, fibrin, fibronectin, laminin, derivatives thereof, or other biologic agents or mixtures of any of these.

The therapeutic or pharmaceutical agent can be encapsulated, embedded or suspended in a biocompatible matrix such as a gel. The gel may be a hydrogel which can be dried and re-hydrated. The matrix can be encapsulated by a cover, which could be semipermeable. The cover may be a membrane, sheet, film, tape or any other desired configuration which is semipermeable.

The cover may have a plurality of holes, pores, slits, or can be formed from a porous network of fibrils, or from a variable density fibril matte, or any other desired perforations. The therapeutic or pharmaceutical agent can be uniformly delivered over a period of time t. Alternatively, the therapeutic or pharmaceutical agent is released at a rate independent of time and the concentration of the pharmaceutically active agent incorporated in the present device. Zero-order release ensures that a steady amount of drug is released over desired length of time, minimizing potential peak/trough fluctuations and side effects, while maximizing the amount of time the drug concentrations remain within the therapeutic window.

The layer incorporating the therapeutic or pharmaceutical agent may be a coating on the exterior surface of the lamina cover. The layer incorporating the agent may also be wrapped around the lamina cover using a spiral tape configuration. The layer or coating from the agent loaded matrix can be applied to the lamina cover using standard techniques to cover the entire or partial surface of the lamina cover. The coating may be a single layer of a homogenous mixture of drugs and a matrix, or in a composition dot matrix pattern. The lamina cover may be dipped or sprayed with a liquid solution comprising at least one pharmaceutical or therapeutic agent. After each layer is applied, the lamina cover is dried before application of the next layer. The thickness of the layer incorporating the therapeutic or pharmaceutical agent may range from about 0.1 μm to about 150 μm, from about 1 μm to about 100 μm, from about 10 μm to about 50 μm, or from about 20μ to 30 μm. Alternatively, multiple layers of the active agent/matrix composition can be applied on the surface of the cover in these thickness ranges. For example, multiple layers of various pharmaceutically active agents can be deposited onto the cover so that a particular drug can be released at one time.

The layer or coating incorporating the pharmaceutical agent may also comprise a matrix. The matrix may comprise a water soluble material or water-swellable material. The therapeutic or pharmaceutical agent may be dispersed within the matrix or coated on the exterior and/or interior surfaces of the matrix. Water soluble material refers to material that dissolves, hydrolyzes, breaks down or disintegrates in contact with water or aqueous physiological fluid, such as blood and interstitial fluid. As the water soluble material layer dissolves, the therapeutic or pharmaceutical agent is released. The length of time that is needed for the water soluble material to be dissolved may be less than 2 hours, less than 1 hour, less than 30 minutes, less than 10 minutes, less than 5 minutes, or less than 1 minute.

The matrix may comprise a mixture of water insoluble and water soluble materials. Examples of the combinations include shellac and olyvinylpyrollidone, and ethyl cellulose and hydroxypropylmthyl cellulose. The matrix may also comprise water swellable material. Water soluble or water swellable material may comprise a polysaccharide, such as dextral, alginate, amylose, amylopectin, carrageenan, carboxylmethyl cellulose, gellan, guar gum, polysaccharide conjugate vaccines, hydroxylethyl cellulose, amylopectin, starch derivatives, hyaluronic acid, starch derivatives, xantan, xyloglucan, chitosan-based hydrogel, peptidoglycan, and progeogl yeans. Water soluble or water swellable material may also comprise a simple carbohydrate, such as glucose, maltose, lactose, fructose, sucrose, galactose, e glucosamine, galactosamine, muramic acid, glucruronate, gluconate, fructose, trehalose, a synthetic polymer, such as polyvinyl alcohol, polyvinylpyrrolindone, polyethylene glycol, propylene glycol, polyoxyethylene derivatives, a polypeptide, such as elastin, polyvinyl amine or poly(L-lysine), uncrosslinked hydrogel, crosslinked hydrogel, polyacrylic acid or any other cross-linked water swellable polymers. Examples of hydrogel materials include carboxymethyl cellulose (CMC), hydroxypropylmethyl cellulose (HPMC), amylopectin, starch derivatives, hyaluronic acid, or their combinations.

The matrix that incorporates the pharmaceutically active agent may also comprise many desired biocompatible, non-toxic material. Examples of biocompatible materials include poly(lactide-co-glycolide), polyesters such as polylactic acid, polyglycolic acid, polyanhydride, polycaprolactone, polyhydroxybutyrate valerate, or mixtures of copolymers thereof. In one embodiment, the matrix may further comprise naturally occurring substances such as collagen, fibronectin, vitronectin, elastin, laminin, heparin, fibrin, cellulose, carbon or extracellular matrix components. Polymers which can be used in the matrix include poly(lactic-co-glycolide); poly-DL-lactide, poly-L-lactide, and/or mixtures thereof and can be of various inherent viscosities and molecular weights. In one embodiment, poly(DL lactide-co-glycolide) can be used. The poly-DL-lactide material can be in the form of homogenous composition and when solubilized and dried, it can form a lattice of channels in which pharmaceutical or therapeutic substances can be trapped for delivery to the tissues. In a further embodiment, the coating composition comprises a nonabsorbable polymer, such as ethylene vinyl acetate (EVAC), polybutyl-methacrylate (PBMA) and methylmethacrylate (MMA).

The matrix may also comprise an organogel, such as poly(ethylene), L-alanine, sorbitan monostearate, Eudragit or lecithin organogel. Alternatively, the gels may comprise a sol-gel. In another embodiment, the matrix may comprise a tape such as bioadhesive which can be wrapped around the lamina cover. For example, an alkyl cyanoacrylate monomer which polymerizes into a thin flexible film may be used. Alkyl chain cyanoacrylates such as methyl-, ethyl-, isopropyl, butyl and octylcyanoacrylate may be used. Other possible bioadhesives include, urethane-based materials as well as adhesives incorporating mussel adhesive proteins.

The layer or coating incorporating the therapeutic or pharmaceutical agent may be dispersed within and or onto a sponge-like membrane or layer, made of a non-hydrogel polymer having a plurality of voids. The sponge like membrane or layer alternatively may also be constructed out of a polymer based fiberal network or scaffolding, resulting in void spaces existing within this fiberous or fiberal nodal network. The therapeutic or pharmaceutical agent is infused into the voids of the sponge membrane or layer that overlies that lamina cover. The therapeutic or pharmaceutical agent is expelled through the voids of the sponge membrane or layer. The sponge membrane or layer may be prepared by dissolving a non-hydrogel polymer in a solvent and an elutable particulate material. After the sponge membrane or layer composition is cured, it is exposed to a solvent, e.g. water, which causes the particulate material to elute from the polymer, leaving a sponge membrane or layer having a plurality of voids therein. The sponge coating is then exposed to a biologically active material to load the sponge membrane or layer with such material. Such material may be loaded into the coating by diffusion or other means. The non-hydrogel polymer(s) useful for forming the sponge membrane or layer should be ones that are biocompatible. Non-hydrogel polymers are polymers that when a drop of water is added on top of a film of such polymer, the drop will not spread. Examples of such polymers include, without limitation, polyurethanes, polyisobutylene and its copolymers, silicones, and polyesters. Other suitable polymers include polyolefins, polyisobutylene, ethylene-alphaolefin copolymers, High Density High Molecular Weight Polyethelene (HDHMWPE), acrylic polymers and copolymers, vinyl halide polymers and copolymers such as polyvinyl chloride, polyvinyl ethers such as polyvinyl methyl ether, polyvinyl halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxylmethyl cellulose, collagens, chitins, polylactic acid, polyglycolic acid, and polylactic acid-polyethylene oxide copolymers.

The therapeutic or pharmaceutical agent may be incorporated into microspheres, liposomes, and other types of particle-based drug delivery vehicles which are incorporated in the matrix. For example, Poly(lactic-co-glycolic acid) nanoparticles can be incorporated within a cross-linkable hyaluronan-based hydrogel matrix. Alternatively, the matrix may comprise a nanogel for encapsulating the therapeutic or pharmaceutical agent. Nanogels are a polymer network of charged polyionic segments crosslinked by polyethylene glycol (PEG) segments. A wide variety of different pharmaceutical agents can be incorporated into the nanogel.

Examples of anti-restenotic agents include but are not limited to, taxol, a pharmaceutically active taxol derivative, rapamycin, a pharmaceutically active rapamycin derivative, synthetic matrix metalloproteinase inhibitors such as batimastat (BB-94), a cell-permeable myotoxins such as cytochalasin B, gene-targeted therapeutic drugs, c-myc neutrally charged antisense oligonucleotides such as nonpeptide inhibitors such as tirofiban, antiallergic drugs such as tranilast, gene-based therapeutics such as paclitaxel, and combinations thereof).

Examples of anti-fibrotic agents include but are not limited to, an agent that degrades or causes the dissolution or shrinkage of fibrotic tissue or a portion thereof; an agent that enzymatically degrades or shrinks the fibrotic tissue, such as protease or glycanase; a hormone, such as relaxin, which inhibits collagen production and stimulates collagen degradation; a cytokine, drug, cell, or nucleic-acid-based material that influences the function, viability, or proliferation of fibroblasts or other cells in the fibrotic tissue; or cells that inhibit collagen production and/or stimulates collagen degradation. Specific examples of anti-fibrotic agents include alginate, chondroitin sulfate, dermatan sulfate, dextran sulfate, hyaluronic acid, heparin, heparin sulfate, keratin sulfate, and pentose polysulfate, or combinations thereof.

Examples of anti-inflammatory agents (in cases where no spinal fusion is involved, as anti-inflammatory would impede spinal fusion) include but are not limited to naproxen; diclofenac; celcoxib; sulindac; diflunisal; piroxicam; indomethacin; etodolac; meloxical; ibuprofen; ketoprofen; r-flurbiprofen; mefenamic; nabumetone; tolmetin, and sodium sales of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isolers); methyl, ethyl, propyl, isopropyl, n-butyl, sec-butyl, t-butyl, esters of acetylsalicylic acid; tenoxicam; aceclofenac; nimesulide;

nepafenac; amfenac; bromfenac; flufenamate; phenylbutazone, or combinations thereof.

Examples of antibiotics include but are not limited to aminoglycosides such as streptomycin, amikacin, and tobramycin; macrolines such as erythromycin, clarithromycin, and lincomycin; tetracyclines such as tetracycline, dosycycline, chlortetracycline, and minocycline; oxaxolidinones such as linezolid; fusidic acid; and chloramphenicol; beta-lactam penicillins such as penicillin, amoxicillin, dicloxacillin, and ampicillin; beta lactam cephalsporins such as ceftaxime, cefuroxime, cefaclor, and ceftriaxone; beta lacram carbapenems such as impenem and meropenem; quinolones such as ciprofloxacin, moxifloxacin, and levofloxacin; sulfonamides such as sulfanilamide and sulfamethoxazole; metronidazole; rifampin; vancomycin; and nitrofurantoin.

Pharmaceutical agents that may be used in the present invention include: (i) pharmacological agents such as, (a) anti-thrombotic agents such as heparin, heparin derivatives, urokinase, and PPack (dextrophenylalanine proline aginine chloromethylketone); antiinflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, antiostatin, angiopeptin, monoclonal antibodies capable of blocking smooth muscle cell proliferation, thymidine kinase inhibitors, rapamycin, 40-0-2(Hydroxylethyl) rapamycin (everolimus), 40-0-Benzyl-rapamycin, 40-0(4'-Hydroxymethyl)benzyl-rapamycin, 40-0-[4'-(1,2-Dihydroxylethyl)]benzyl-rapamycin, 40-Allyl-rapamycin, 40-0-[3'-92,2-Dimethyl-1,3-dioxolan-4(S)-yl-prop-2'-en-1' yl]-20 rapamycin, (2':E,4'S)-40-0-(4',5'.:Dihydroxypent-2' en-1'yl), rapamycin 40-0(2Hydroxy) ethoxycar-bonylmethyl-rapamycin, 40-0-(3-Hydroxypropyl-rapamycin 40-0-((Hydroxyl)hexyl-rapamycin 40-0-[2-(2-Hydroxy)ethoxy] ethyl-rapamycin, 40-0-[(3S)-(Hydroxy)hexyl-rapamycin 40-0-[2-(2-Hydroxy)ethoxy]ethyl-rapamycin, 40-0-[(3S)-2, 2Dimethyldioxolan-3-yl]methyl-rapamycin, 40-0-(2-Nicotinoloxy)ethyl-rapamycin, 40-0[2-(N-Methyl-N'-piperazinyl) acetoxy]ethyl-rapamycin, 39-0-Desmethyl-3.9,400-0,0 ethylene-rapamycin, (26R)-26-Dihydro-40-0-(2-hydroxy) ethyl-rapamycin, 28-O Methyrapamycin, 40-0-(2-Aminoethyl)-rapamycin, 40-0-(2-Acetaminoethyl)-rapamycin 40-0 (2-Nicotinamidoethyl)-rapamycin, 40-0-(3-(N-Methylimidazo-2'ylcarbcthoxamido)ethyl)-30 rapamycin, 40-0-(2-Ethoxycarbonylaminoethyl)-rapamycin, 40-0-(2-Tolylsulfonamidoethyl)-rapamycin, 40-0-(2-Ethoxycarbonylaminoethyl)-rapamycin, 40-0-(2-Tolylsulfonaminoethyl)-rapamycin, 40-0-[2-(4',5'-Dicarboethoxy-1',2',3'-triazol-1'-yl0-ethyl]rapamycin, 42-Epi-(telrazolyl) rapamycin (tacrolimus), and 42-[3-hydroxy-2-(hydroxymethyl)-3-methylpropanoate] rapamycin (temsirolimus), (d) anesthetic agents such as lidocaine, bupivacaine and ropivacaine; € anti-coagulants such as D-Phe-Pro-Arg chloromethyl ketone, and RGD peptide containing compound, heparin, hirudin, antithrombin compounds, platelet receptor antagonists, antithrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrophostins, genistein, quinoxalines); (i) prostacyclin analogs; (j) cholesterol-lowering agents; (k) angiopoietins; (l) antimicrobial agents such as triclosan, cephalosporin, aminoglycosides and nitrofurantoin; m) cytotoxic agents, cytostatic agents and cell proliferation affectors; (n) vasodilating agents; and, (o) agents that interfere with endogenous vasoactive mechanism, (ii) genetic therapeutic agents include anti-sense DNA and RNA as well as DNA coding for (a) anti-sense RNA, (b) tRNA or rRNA to replace defective or basic fibroblast growth factors, vascular endothelial growth factor, epidermal growth factor, transforming growth factor a and P, platelet-derived endothelial growth factor, platelet-derived growth factor, tumer necrosis factor a, hepatocyte growth factor and insulin-like growth factor, (d) cell cycle inhibitors including CD inhibitors, and € thymidine kinase ("TK" and other agents useful for interfering with cell proliferation.

Other pharmaceutical agents that can be used, include, acarbosc, antigens, beta-receptor blockers, non-steroidal anti-inflammatory drugs (NSAID, cardiac glycosides, acetylsalicylic acid, virustatics, aclarubicin, acyclovir, cisplatin, actinomycin, alpha- and beta-sympatomimetrics, (dmeprazole, allopurinol, alprostadil, prostaglandins, amantadine, ambroxol, amlodipine, methotrexate, S-aminosaslicylic acid, amitriptyline, amoxicillin, anastrozole, atenolol, azathioprine, balsalazine, beclomcthasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidinc, coytimoxazole, codeine, caffeine, vitamin D and derivatives of vitamin D, colestyramine, cromoglicic acid, coumarin and coumarin derivatives, cysteine, cytarabine, cyclophosamide, cyclosporine, cyproterone, cytabarine, dapiprazole, desogestrel, desonide, dihydralazine, diltiazem, ergot alkaloids, dimenhydrinate, dimethyl sulphoxide, dimeticone, domperidone and domperidan derivatives, doxazosin, doxorubizin, doxylamine, dapiprazole, benzodiazepines, diclofenac, gltcoside antibiotics, desipramine, econazole, ACE inhibitors, enalapril, ephedrine, epinephrine, epoetin and epoetin derivatives, morphinans, calciu antagonists, irinotecan, modafmil, orlistat, peptide antibiotics, phenyltoin, riluzoles, risedronate, sildenafil, topiramatc, macrolide antibiotics, oestrogen and oestrogen derivatives, progestogen and progestogen derivatives, testosterone and testosterone derivatives, androgen and androgen derivatives, ethenzamide, etofenamate, ctofibrate, fenofibrate, etofylHne, etoposide, famciclovir, famotidine, felodipine, fenoftbrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, foromoterol, fosfomicin, furosemide, fusidic acid, gallopamin, ganciclovir, gemfibrozil, gentamicin, ginko, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indomethacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, Lisinopril, lisuride, lofepramine, lomustine, loperamide, loratadine, maprotiline, mebendazole, mebeverine, meclizine, mefenamic acid, mefloquine, meloxicam, mcpindolol, meprobamate, meropenem, mesalazinc, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastinc, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxaqcillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozine, pindolol, piperazine, piracetam, pirenzepine, piribedil, piroxicam, pramipexole, pravastin, prazosin, procaine, promazine, propiverine, propranolol, propyphenazone, prostaglandins, protionamide, proxyphylline, quetiapine, quinapril, quinaprilat, Ramipril, rantidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindone, sertralion, silicates, sildenafil, simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiridine, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclin, teryzoline, theobromine, theophylline, burizine, thiamazole, phenothiazines, thiotepa, tiagabine, tiapride, propionic acid derivatives, ticlopidine, timolol, tinidazol, tioconazole, tioguanine, tioxolone, tiropramide, tizanidine, tolazolinc, tolbutamide, tolcapone, tolnaftate, tolperisone, topotecan, torasemide, antioestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobutcrol, tyramine, tyrothracin, urapidil, ursodeoxycholic acid, chemodeoxycholic acid, valacirclovir, valproic acid, vancomycin, vecuronium chloride, Viagra, venlafaxine, verapamil, vidarabine, vigabatrine, viloazine, vinblastine, vincamine, vincristine, vindesine, vinorelbine, vinpocetine, viquidil, warfarin, xantinol nicotinate, xipamide, zafirlukast, zalcitabine, zidobudine, zolmitriptan, Zolpidem, zoplicone, zotipine and the like.

While the invention has been particularly shown and described with reference to particular embodiments, it will be appreciated that variations of the above-disclosed and other features and functions, or alternatives thereof, may be desirably combined into many other different systems or applications. Also, various alternatives, modifications, variations or improvements therein may be apparent to and may subsequently made by those skilled in the art which are also intended to be encompassed by the following claims.

What is claimed is:

1. A surgical kit comprising:
    a bone fixation assembly, wherein the bone fixation assembly is adapted to be fixated on two vertebra bones of a subject, and wherein the bone fixation assembly comprises at least two vertebra joining members each adapted to be respectively secured between two bone anchors;
    a coupling element adapted to engage a vertebra joining member at a position between the two bone anchors, wherein the coupling element comprises (a) at least two side hooks configured to removably attach to the vertebra joining member, and (b) at least two connecting members disposed between the two hooks, the at least two connecting members slidably connected to each other; and
    a shield for covering a portion of the spine of the subject, wherein the shield includes an attachment portion adapted to engage the coupling element, and wherein the shield includes a single body configured to generally extend in a direction of the spine, the body having a length suitable for protecting at least a portion of one or more of the multiple vertebra bones.

2. The surgical kit of claim 1, each of the two bone anchors comprising a fastener portion adapted to be implanted into a vertebra bone and a head coupling portion adapted to secure one of the two vertebra joining members.

3. The surgical kit of claim 1, wherein the shield has a vertical length to cover at least two vertebrae.

4. The surgical kit of claim 1, wherein the shield comprises an elongated concavity.

5. The surgical kit of claim 1, wherein the attachment portion includes two parts extending laterally on opposite sides of the shield.

6. The surgical kit of claim 1, wherein the shield is made from a polymeric material.

7. The surgical kit of claim 1, wherein the shield is made from a material comprising PEEK.

8. The surgical kit of claim 1, wherein the shield further comprises at least one therapeutic agent selected from the group consisting of an anti-stenotic agent, an anti-fibrotic agent, an anti-inflammatory, an antibiotic agent, and combinations thereof.

9. The surgical kit of claim 8, wherein the at least one therapeutic agent is embedded in a biocompatible matrix.

10. The surgical kit of claim 9, wherein the matrix further comprises a water-soluble material.

11. A shield for covering a portion of the spine of a subject, wherein the shield is fixed to a bone fixation assembly by an attachment portion, wherein the attachment portion is removably attached to a coupling element, wherein the coupling element is adapted to engage two vertebra joining members of the bone fixation assembly at a position between two bone anchors that the two vertebra joining members are secured between, and wherein the shield includes a single body configured to generally extend in a direction of the spine, the body having a length suitable for protecting at least a portion of one or more of multiple vertebra bones of the subject,
    wherein the coupling element comprises (a) at least two side hooks configured to removably attach to the vertebra joining member, and (b) at least two connecting members disposed between the two hooks, the at least two connecting members slidably connected to each other,
    wherein the bone fixation assembly is adapted to be fixated on two vertebra bones of a subject.

12. The shield of claim 11, wherein the bone fixation assembly comprises a bone screw.

13. The shield of claim 11, wherein the vertebra joining member is a rod.

14. A shield for covering a portion of the spine of a subject, comprising:
(a) a coupling element adapted to engage two vertebra joining members of a bone fixation assembly adapted to be fixated on two vertebra bones of the subject, wherein the bone fixation assembly comprises the two vertebra joining members that are each adapted to be respectively secured between two bone anchors, wherein the coupling element is adapted to engage the two vertebra joining members at a position between the two bone anchors, wherein the coupling element comprises (a) at least two side hooks configured to removably attach to the vertebra joining member, and (b) at least two connecting members disposed between the two hooks, the at least two connecting members slidably connected to each other; and (b) a shield portion for covering a portion of the spine, the shield portion being adapted to engage the coupling element, and wherein the shield portion includes a single body that is configured to generally extend in a direction of the spine, the shield portion having a length suitable for protecting at least a portion of one or more of the multiple vertebra bones.

\* \* \* \* \*